US011187698B2

(12) United States Patent
Strano et al.

(10) Patent No.: US 11,187,698 B2
(45) Date of Patent: Nov. 30, 2021

(54) SENSOR FOR INFRARED COMMUNICATION USING PLANT NANOBIONICS

(71) Applicant: MASSACHUSETTS INSTITUTE OF TECHNOLOGY, Cambridge, MA (US)

(72) Inventors: Michael S. Strano, Lexington, MA (US); Juan Pablo Giraldo Gomez, Claremont, CA (US); Seongyeon Kwak, Cambridge, MA (US); Min Hao Wong, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 510 days.

(21) Appl. No.: 15/781,123

(22) PCT Filed: Dec. 2, 2016

(86) PCT No.: PCT/US2016/064847
§ 371 (c)(1),
(2) Date: Jun. 2, 2018

(87) PCT Pub. No.: WO2017/096317
PCT Pub. Date: Jun. 8, 2017

(65) Prior Publication Data
US 2018/0356404 A1 Dec. 13, 2018

Related U.S. Application Data

(60) Provisional application No. 62/262,892, filed on Dec. 3, 2015.

(51) Int. Cl.
*G01N 15/06* (2006.01)
*G01N 21/00* (2006.01)
(Continued)

(52) U.S. Cl.
CPC .......... *G01N 33/5097* (2013.01); *A01H 5/00* (2013.01); *G01N 33/542* (2013.01);
(Continued)

(58) Field of Classification Search
CPC ............. G01N 33/5097; G01N 33/542; G01N 33/54346; G01N 33/566; G01N 15/06;
(Continued)

(56) References Cited

U.S. PATENT DOCUMENTS 4,080,442 A * 3/1978 Mizutani ................ A61K 31/70
514/53
9,664,677 B2 5/2017 Strano et al.
(Continued)

OTHER PUBLICATIONS

International Preliminary Report on Patentability dated Jun. 14, 2018 for PCT/US2016/064847.
(Continued)

*Primary Examiner* — Brian J. Sines
(74) *Attorney, Agent, or Firm* — Honigman LLP

(57) ABSTRACT

A living plant can function as self-powered auto-samplers and preconcentrators of an analyte within ambient groundwater, detectors of the analyte contained therein. For example, a pair of near infrared (IR) fluorescent sensors embedded within the mesophyll of the plant leaf can be used as detectors of the nitroaromatic molecules, with the first IR channel engineered through CoPhMoRe to recognize analyte via an IR fluorescent emission and the second IR channel including a functionalized nanostructure that acts as an invariant reference signal.

43 Claims, 21 Drawing Sheets

(51) Int. Cl.
  *G01N 21/64* (2006.01)
  *G01N 33/50* (2006.01)
  *A01H 5/00* (2018.01)
  *G01N 33/543* (2006.01)
  *G01N 33/566* (2006.01)
  *G01N 33/542* (2006.01)

(52) U.S. Cl.
  CPC ..... *G01N 33/54346* (2013.01); *G01N 33/566* (2013.01); *G01N 2400/10* (2013.01); *G01N 2405/04* (2013.01)

(58) Field of Classification Search
  CPC ........ G01N 33/00; G01N 33/48; G01N 21/00; G01N 21/64
  See application file for complete search history.

(56) References Cited

U.S. PATENT DOCUMENTS

| | | | | |
|---|---|---|---|---|
| 2007/0191932 | A1* | 8/2007 | Kutryk | A61F 2/82 623/1.38 |
| 2011/0257033 | A1 | 10/2011 | Strano et al. | |
| 2011/0269243 | A1* | 11/2011 | Strano | G01N 21/6428 436/172 |
| 2013/0143769 | A1* | 6/2013 | Afzali-Ardakani | G01N 33/551 506/15 |
| 2013/0230464 | A1* | 9/2013 | Yi | A61K 49/0056 424/9.6 |
| 2015/0047074 | A1* | 2/2015 | Strano | A01H 5/00 800/298 |
| 2018/0317415 | A1* | 11/2018 | Strano | C12N 9/0069 |
| 2018/0356414 | A1* | 12/2018 | Strano | G01N 33/531 |

OTHER PUBLICATIONS

International Search Report and Written Opinion dated Apr. 13, 2017 for PCT/US2016/064847.

Wei et al. Minatureized Paper-Based Gene Sensor for Rapid and Sensitive Identification of Contagious Plant Virus. ACS Appl. Mater. Interfaces, 6(24), 22577-22584, 2014.

Wang et al, Two-Photon Sensing and Imaging of Endogenous Biological Cyanide in Plant Tissues Using Graphene Quantum Dot/Gold Nanoparticle Conjugate. ACS Appl. Mater. Interfaces, 7(34), 19509-19515, 2015.

* cited by examiner

SENSOR FOR INFRARED COMMUNICATION USING PLANT NANOBIONICS

CLAIM OF PRIORITY

This application claims the benefit under 35 USC 371 to International Application No. PCT/US2016/064847, filed Dec. 2, 2016, which claims the benefit of prior U.S. Provisional Application No. 62/262,892, filed on Dec. 3, 2015, each of which is incorporated by reference in its entirety.

GOVERNMENT SPONSORSHIP

This invention was made with Government support under Contract No. DE-FG02-08ER46488 awarded by the U.S. Department of Energy. The Government has certain rights in the invention.

FIELD OF INVENTION

This invention relates to nanobionic engineering of photosynthetic organisms.

BACKGROUND

Plant nanobionics is the use of specifically designed and targeted nanoparticles to engineer living plants with non-native functions. As independent energy sources, plants are adapted for persistence and self-repair in harsh environments with negative carbon footprints. See Giraldo, J. P. et al. Plant nanobionics approach to augment photosynthesis and biochemical sensing. *Nat Mater* 13, 400-408, doi: 10.1038/nmat3890 (2014), which is incorporated by reference in its entirety.

A eukaryotic cell is a cell that contains membrane-bound organelles, most notably a nucleus. An organelle is a specialized subunit within a cell that has a specific function, and can be separately enclosed within its own lipid bilayer. Examples of organelles include mitochondria, chloroplasts, Golgi apparatus, endoplasmic reticulum, and as previously mentioned, the nucleus. Organelles are found within the cell cytoplasm, an intracellular fluid that is separated from extracellular fluid by the plasma membrane. The plasma membrane is a double layer (i.e., a bilayer) of phospholipids that permits only certain substances to move in and out of the cell.

In addition to these features, plant cells include specialized organelles that are not generally found in animal cells. For example, plant cells include a rigid cell wall. Plant cells also include chloroplasts. Chloroplasts are chlorophyll-containing double-membrane bound organelles that perform photosynthesis. Chloroplasts are believed to be descendants of prokaryotic cells (e.g., cyanobacteria) that were engulfed by a eukaryotic cell.

SUMMARY OF THE INVENTION

A sensor for an analyte can include a first channel including a first complex including a nanoparticle and a first polymer, wherein the first channel detects a stimulus within a plant, and a second channel including a second complex including a nanoparticle and a second polymer, wherein the second channel detects a reference property within the plant. In certain embodiments, a green plant can include such a sensor.

In certain embodiments, the first polymer adsorbed on the nanostructure can have a selective binding site and the polymer is free from selective binding to an analyte in the absence of being adsorbed on the nanostructure.

In certain embodiments, the nanostructure can be a photoluminescent nanostructure. The photoluminescent nanostructure can be a nanotube, a carbon nanotube, a single-walled carbon nanotube, or graphene.

In certain embodiments, the first polymer can be Bombolitin.

In certain embodiments, the first polymer can be a polysaccharide. The polysaccharide can include dextran, a functionalized dextran, phenoxy functionalized dextran, or boronic acid functionalized phenoxy dextran.

In certain embodiments, the first polymer can be a polynucleotide. The polynucleotide can have an ordered sequence, or can be poly(AT), poly(GT), poly(CT), poly(AG), poly(CG), or poly(AC).

In certain embodiments, the first polymer can be a polypeptide. The polypeptide can include a mastoparan, mastoparan 7, or mastoparan X.

In certain embodiments, the first polymer can be a polylipid. The polylipid can include a phospholipid, a palmitoyl phospholipid, or 1,2-dipalmitoyl-sn-glycero-3-phosphoethanolamine-N-(lauroyl).

In certain embodiments, the first polymer can be polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In certain embodiments, the first polymer can be a dye conjugate or a branched polymer.

In certain embodiments, the second polymer can be polyvinylpyrrolidone, poly(ethylene oxide)-poly(propylene oxide)-poly(ethylene oxide) block co-polymer, a poly(ethylene oxide), poly(N-isopropyl acrylamide), polyethyleneimine, polyacrylamide, polyvinyl alcohol or collagen.

In certain embodiments, the stimulus can be a concentration of the analyte.

In certain embodiments, the analyte can be a monosaccharide, a polysaccharide, an amino acid, a nucleotide, an oligonucleotide, a lipid, a polylipid, a steroid, a peptide, a protein, riboflavin, nitric oxide, or nitroaromatic. In certain embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramine, urea, or picric acid.

In certain embodiments, the plant can be a wild-type plant.

A method for analyzing a sample for an analyte can include providing a sensor comprising a first channel including a first complex including a nanoparticle and a first polymer, wherein the first channel detects a stimulus within a plant and a second channel including a second complex including a nanoparticle and a second polymer, wherein the second channel detects a reference property within the plant, exposing the sensor to a sample, monitoring a first signal of the first channel and a second signal of the second channel, and determining a presence of the analyte in the sample based on the first signal and the second signal.

In certain embodiments, the first polymer adsorbed on the nanostructure can have a selective binding site and the polymer is free from selective binding to an analyte in the absence of being adsorbed on the nanostructure.

In certain embodiments, the nanostructure can be a photoluminescent nanostructure. The photoluminescent nanostructure can be a nanotube, a carbon nanotube, a single-walled carbon nanotube, or graphene.

In certain embodiments, the first polymer can be Bombolitin.

In certain embodiments, the first polymer can be a polysaccharide. The polysaccharide can include dextran, a functionalized dextran, phenoxy functionalized dextran, or boronic acid functionalized phenoxy dextran.

In certain embodiments, the first polymer can be a polynucleotide. The polynucleotide can have an ordered sequence, or can be poly(AT), poly(GT), poly(CT), poly (AG), poly(CG), or poly(AC).

In certain embodiments, the first polymer can be a polypeptide. The polypeptide can include a mastoparan, mastoparan 7, or mastoparan X.

In certain embodiments, the first polymer can be a polylipid. The polylipid can include a phospholipid, a palmitoyl phospholipid, or 1,2-dipalmitoyl-sn-glycero-3-phosphoethanolamine-N-(lauroyl).

In certain embodiments, the first polymer can be polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In certain embodiments, the first polymer can be a dye conjugate or a branched polymer.

In certain embodiments, the second polymer can be polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In certain embodiments, the stimulus can be a concentration of the analyte.

In certain embodiments, the analyte can be a monosaccharide, a polysaccharide, an amino acid, a nucleotide, an oligonucleotide, a lipid, a polylipid, a steroid, a peptide, a protein, riboflavin, nitric oxide, or nitroaromatic. In certain embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramine, urea, or picric acid.

In certain embodiments, the plant can be a wild-type plant.

In certain embodiments, the sample can include a gas, a liquid or a solid. In certain embodiments, the sample can be a ground water. In certain embodiments, the sample can be a biological fluid.

In certain embodiments, the first signal can be an emission, emission intensity, or an emission wavelength. In certain embodiments, the emission can be infrared (IR) fluorescent emission. In certain embodiments, the second signal can be an emission, emission intensity, or an emission wavelength. In certain embodiments, the emission can be infrared (IR) fluorescent emission.

In certain embodiments, exposing the composition to a sample can include inserting the composition into an animal, a plant, or a fungus. In certain embodiments, exposing the composition to a sample can include incubating the composition with a microorganism, a virus, a cell line, or an in vitro model system.

In certain embodiments, determining the presence of an analyte can include determining the absence of the analyte, or determining the concentration of the analyte.

In certain embodiments, monitoring the first signal of the first channel and the second signal of the second channel can be performed using a high-throughput system.

In certain embodiments, the composition can be exposed to a sample in a well in a well plate array.

In certain embodiments, monitoring the first signal of the first channel and the second signal of the second channel can be executed by a satellite. In certain embodiments, monitoring the first signal of the first channel and the second signal of the second channel is executed from a distance of several meters, tens of meters, or hundreds of meters.

In certain embodiments, the first signal and second signal can be sent to a cell phone.

A method for analyzing a sample for a plurality of analytes can include providing a plurality of sensors, wherein each sensor including a first channel including a first complex including a nanoparticle and a first polymer, wherein the first channel detects a stimulus within a plant and a second channel including a second complex including a nanoparticle and a second polymer, wherein the second channel detects a reference property within the plant, exposing the plurality of the sensors to a sample, monitoring a first signal of the first channel of the each sensor and a second signal of the second channel of the each sensor, and determining a presence of each analyte in the sample based on the first signal and the second signal of the each sensor.

A sensor for an analyte can include a first channel including a first complex including graphene and a first polymer, wherein the first channel detects a stimulus within a plant, and a second channel including a second complex including graphene and a second polymer, wherein the second channel detects a reference property within the plant. In certain embodiments, a green plant can include such a sensor.

In certain embodiments, the first polymer adsorbed on the graphene can have a selective binding site and the polymer is free from selective binding to an analyte in the absence of being adsorbed on the graphene.

In certain embodiments, the first polymer can be Bombolitin.

In certain embodiments, the first polymer can be a polysaccharide. The polysaccharide can include dextran, a functionalized dextran, phenoxy functionalized dextran, or boronic acid functionalized phenoxy dextran.

In certain embodiments, the first polymer can be a polynucleotide. The polynucleotide can have an ordered sequence, or can be poly(AT), poly(GT), poly(CT), poly (AG), poly(CG), or poly(AC).

In certain embodiments, the first polymer can be a polypeptide. The polypeptide can include a mastoparan, mastoparan 7, or mastoparan X.

In certain embodiments, the first polymer can be a polylipid. The polylipid can include a phospholipid, a palmitoyl phospholipid, or 1,2-dipalmitoyl-sn-glycero-3-phosphoethanolamine-N-(lauroyl).

In certain embodiments, the first polymer can be polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In certain embodiments, the first polymer can be a dye conjugate or a branched polymer.

In certain embodiments, the second polymer can be polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In certain embodiments, the stimulus can be a concentration of the analyte.

In certain embodiments, the analyte can be a monosaccharide, a polysaccharide, an amino acid, a nucleotide, an oligonucleotide, a lipid, a polylipid, a steroid, a peptide, a protein, riboflavin, nitric oxide, or nitroaromatic. In certain embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramine, urea, or picric acid.

In certain embodiments, the plant can be a wild-type plant.

A method for analyzing a sample for an analyte can include providing a sensor comprising a first channel including a first complex including graphene and a first polymer, wherein the first channel detects a stimulus within a plant and a second channel including a second complex including graphene and a second polymer, wherein the second channel detects a reference property within the plant, exposing the sensor to a sample, monitoring a first signal of the first channel and a second signal of the second channel, and determining a presence of the analyte in the sample based on the first signal and the second signal.

In certain embodiments, the first polymer adsorbed on the graphene can have a selective binding site and the polymer is free from selective binding to an analyte in the absence of being adsorbed on the graphene.

In certain embodiments, the first polymer can be Bombolitin.

In certain embodiments, the first polymer can be a polysaccharide. The polysaccharide can include dextran, a functionalized dextran, phenoxy functionalized dextran, or boronic acid functionalized phenoxy dextran.

In certain embodiments, the first polymer can be a polynucleotide. The polynucleotide can have an ordered sequence, or can be poly(AT), poly(GT), poly(CT), poly (AG), poly(CG), or poly(AC).

In certain embodiments, the first polymer can be a polypeptide. The polypeptide can include a mastoparan, mastoparan 7, or mastoparan X.

In certain embodiments, the first polymer can be a polylipid. The polylipid can include a phospholipid, a palmitoyl phospholipid, or 1,2-dipalmitoyl-sn-glycero-3-phosphoethanolamine-N-(lauroyl).

In certain embodiments, the first polymer can be polyvinylpyrrolidone, poly(ethylene oxide)-poly(propylene oxide)-poly(ethylene oxide) block co-polymer, a poly(ethylene oxide), poly(N-isopropyl acrylamide), polyethyleneimine, polyacrylamide, polyvinyl alcohol or collagen.

In certain embodiments, the first polymer can be a dye conjugate or a branched polymer.

In certain embodiments, the second polymer can be polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

In certain embodiments, the stimulus can be a concentration of the analyte.

In certain embodiments, the analyte can be a monosaccharide, a polysaccharide, an amino acid, a nucleotide, an oligonucleotide, a lipid, a polylipid, a steroid, a peptide, a protein, riboflavin, nitric oxide, or nitroaromatic. In certain embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramine, urea, or picric acid.

In certain embodiments, the plant can be a wild-type plant.

In certain embodiments, the sample can include a gas, a liquid or a solid. In certain embodiments, the sample can be a ground water. In certain embodiments, the sample can be a biological fluid.

In certain embodiments, the first signal can be an emission, emission intensity, or an emission wavelength. In certain embodiments, the emission can be infrared (IR) fluorescent emission. In certain embodiments, the second signal can be an emission, emission intensity, or an emission wavelength. In certain embodiments, the emission can be infrared (IR) fluorescent emission.

In certain embodiments, exposing the composition to a sample can include inserting the composition into an animal, a plant, or a fungus. In certain embodiments, exposing the composition to a sample can include incubating the composition with a microorganism, a virus, a cell line, or an in vitro model system.

In certain embodiments, determining the presence of an analyte can include determining the absence of the analyte, or determining the concentration of the analyte. In certain embodiments, monitoring the first signal of the first channel and the second signal of the second channel can be performed using a high-throughput system.

In certain embodiments, the composition can be exposed to a sample in a well in a well plate array.

In certain embodiments, monitoring the first signal of the first channel and the second signal of the second channel can be executed by a satellite. In certain embodiments, monitoring the first signal of the first channel and the second signal of the second channel is executed from a distance of several meters, tens of meters, or hundreds of meters.

In certain embodiments, the first signal and second signal can be sent to a cell phone.

A method for analyzing a sample for an analyte can include providing a plurality of sensors, wherein each sensor including a first channel including a first complex including graphene and a first polymer, wherein the first channel detects a stimulus within a plant and a second channel including a second complex including graphene and a second polymer, wherein the second channel detects a reference property within the plant, exposing the plurality of the sensors to a sample, monitoring a first signal of the first channel of the each sensor and a second signal of the second channel of the each sensor, and determining a presence of the analyte in the sample based on the first signal and the second signal of the each sensor.

Other aspects, embodiments, and features will be apparent from the following description, the drawings, and the claims

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1A shows a schematic of a plant functioning as a fluidic device and sampler of the environment. FIG. 1B are images showing SWCNTs are trapped within the parenchyma tissues.

FIG. 2A shows diagrammatic depiction of standoff detection set-up with the nanobionic sensing plant. FIG. 2B shows brightfield image of spinach plant leaf infiltrated with SWCNT and under 785 nm excitation. FIG. 2C shows SWCNT nIR emission similarly detected by a RaspeberryPi® CCD detector (IR filters removed) which then transmit pictures wirelessly and in real time via email interface to a smartphone.

FIG. 3A is a graph depicting plants exposed to the control solution did not show a substantial quenching for both B-SWCNTs and P-SWCNTs. FIG. 3B is a graph depicting picric acid leads to a steady decline in nIR fluorescence of B-SWCNT while P-SWCNT fluorescence was stable. FIG. 3C is a graph depicting monitoring of the B-SWCNT/P-SWCNT ratio showed a clear quenching for plants that were exposed to Picric acid. FIG. 3D is a graph depicting two-tailed P value of 0.0061 indicates a statistically significant difference between the control samples and the samples that were exposed to picric acid. FIG. 3E shows monitoring of the B-SWCNT/P-SWCNT ratio using a Raspberry Pi CCD detector (no IR filters) similarly showed a clear quenching for plants that were exposed to Picric acid (time lapse figures as in FIG. 2C). FIG. 3F shows $(GT)_{15}$-SWCNT emission spectra tracked with time as plants transpire a solution of 100 μM of dopamine. FIG. 3G shows a turn on response of approximately 10% seen as spinach plants transpire a solution of 100 μM of dopamine. FIG. 3H shows a plant modelled as a sequence of reactors (CSTRs and PFRs) in series with an equivalent RTD. Fitted RTD model lines are shown in FIGS. 3C, 3E and 3G.

FIG. 4A shows nIR image of excised spinach leaf infiltrated with B-SWCNT and P-SWCNT. FIG. 4B shows time series of the nIR fluorescence changes in B-SWCNT and P-SWCNT inside spinach leaves in response to picric acid applied exogenously on the leaf surface. FIG. 4C shows P-SWCNT nIR fluorescence remains unchanged in the presence of picric acid while B-SWCNT intensity quenches by 14%. FIG. 4D shows viability of nanobionic plants after infiltration with Bombolitin-SWCNT, PVA-SWNT, and HEPES buffer (control). FIG. 4E shows the plant acts as a self-powered autosampler of ground water by absorbing analytes and transporting them up the plant via the vascular system.

FIG. 6A shows the experimental procedure. FIG. 6B shows the intensity of B-SWCNT was observed to quench significantly in response to picric acid at the end of an hour.

FIG. 8A shows a schematic of a graphene leaf hybrid material to regulate analyte residence time within leaf while maintaining stomatal activity and may also enable gaseous analyte sensing. FIG. 8B shows a photo of Graphene-PMMA deposited on the abaxial surface of a spinach (*Spinacia oleracea*) leaf (left) as well as on the adaxial surface of a European lily (*Convallaria majalis*) leaf.

FIG. 9A shows photos of stomata of a spinach leaf as observed in the closed and open states, with (left) and without (right) graphene PMMA deposited. FIG. 9B shows a graph depicting stomata aperature monitored at different light conditions and with or without (control) graphene-PMMA.

FIGS. 10A and 10B show photos of the stoma of the peace lily plant seen with (left) and without (right) graphene PMMA deposited in the dark. FIGS. 10C and 10E show photos of plants when exposed to 10 mW/cm² white light lamp for 2 hours. FIG. 10E shows a graph depicting stomata aperature monitored at different light conditions and with or without (control) graphene-PMMA.

DETAILED DESCRIPTION

Figure 1A:
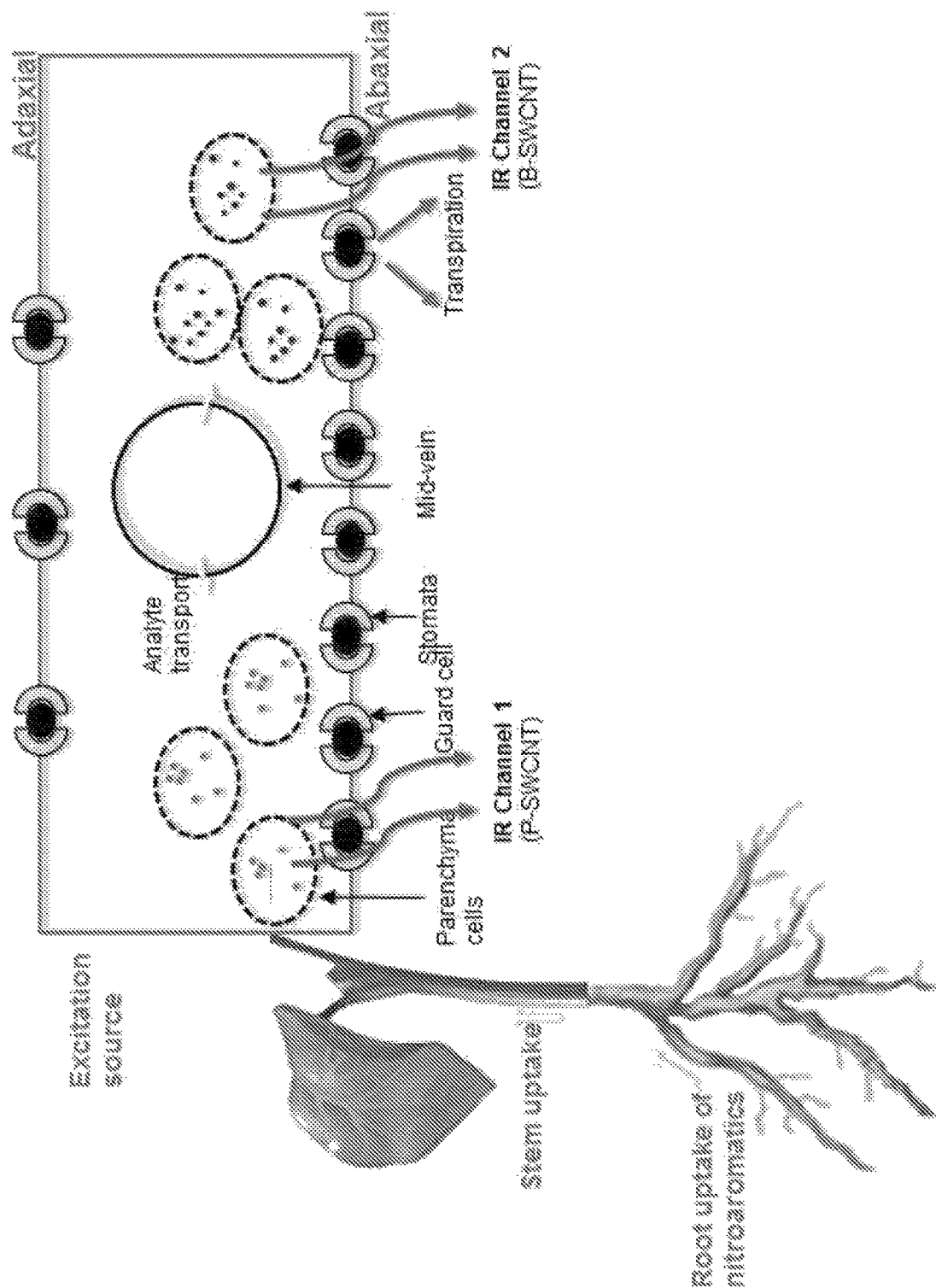
FIGS. 1A-1B show nitroaromatic detection and infrared communication in wild type plants via plant nanobionics.
Figure 1B:
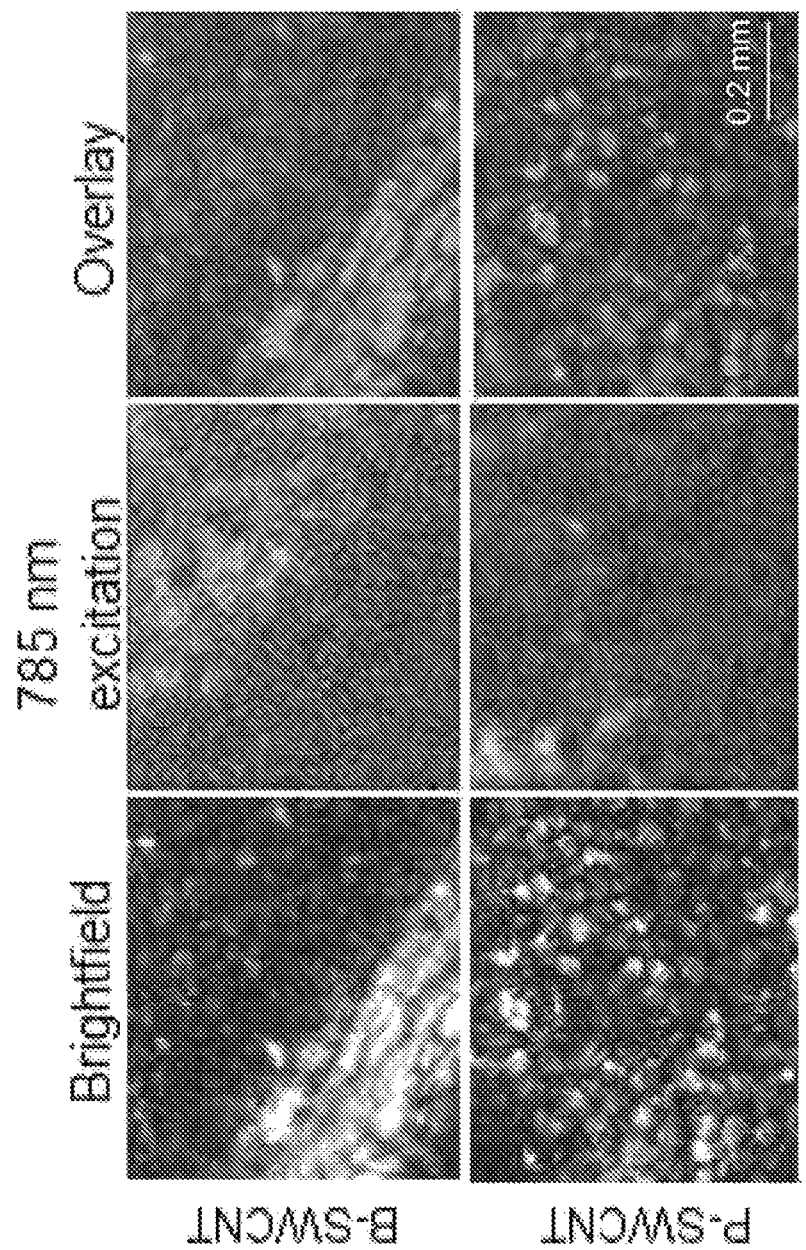

Nanoparticles below 10 nm in dimension are necessarily commensurate in size with the proteins and other macromolecules that comprise living plants, and therefore have potential to introduce non-native and unexpected functionalities such as biochemical sensing abilities into wild type living plants. Throughout the day, plants continually exchange fluids and gases with the environment, serving as a self-powered auto-sampler of their surroundings. Transpiration in plants is characterized by several attributes, including the transduction of subsaturation in the vapor phase of water into negative pressures in the liquid phase, stabilization and flow of liquid water at large negative pressures, continuous heat transfer with the evaporation of liquid water at negative pressure, and the continuous extraction of liquid water from subsaturated sources. See, Wheeler, T. D. & Stroock, A. D. The transpiration of water at engative pressures in a synthetic tree. *Nature* 455, 208-212 (2008), which is incorporated by reference in its entirety. These properties render plants potentially compelling platforms for the extraction and subsequent detection of low concentrations of specific environmental analytes. However, the engineering of naturally occurring, wild type plants as microfluidic, self-powered auto-samplers of their surroundings has not yet been considered. Numerous studies have shown that leaves are the main sinks of airborne particulates such as polycyclic aromatic hydrocarbons (PAH). See, Reischl, A., Reissinger, M., Thoma, H., Hutzinger, O. Uptake and accumulation of PCDD/F in terrestrial plants: basic considerations. *Chemosphere* 19, 467-474 (1989), and Buckley, E. H. Accumulation of airbourne polychlorinated biphenyls in foliage. *Science* 216, 520 (1982), each of which is incorporated by reference in its entirety. Uptake via the stomata appears significant for low volatile (K<10) compounds while for moderately to highly volatile compounds, exchange occurs mainly via the cuticle. See, Riederer, M. Estimating partitioning and transport of organic-chemicals in the foliage atmosphere system—discussion of a fugacity-based model. *Environ. Sci. Technol.* 24 (1990), and McLachlan, M. S. Framework for the interpretation of measurements of SOCs in plants. *Environ. Sci. Technol.* 33, 1799-1804 (1999), each of which is incorrporated by reference in its entirety. The root uptake of organic compounds have also been extensively studied. Su et al found that the uptake of dinitrotoluene and dinitrobenzene is achieved presumably mainly via the symplastic pathway in roots of rice plants. See, Su, Y. & Zhu, Y. Transport mechanisms for the uptake of organic compounds by rice (*Oryza sativa*) roots. *Env. Pollution* 148, 94-100 (2007), which is incorporated by reference in its entirety. These nitroaromatic compounds, which are generally of intermediate polarity, then enter the xylem, where it either adsorbs and accumulates, or get transported to other parts of the plant. Furthermore, several authors have shown that nitroaromatics are taken up by the plant, either under hydroculture conditions or after the addition of TNT to soil. See, McCrady, J., McFarlane, C. & Lindstrom, F. The transport and affinity of substituted benzenes in soybean stems. *J. Exp. Botany* 38, 1875-1890 (1987), Gorge, E., Brandt, S. & Werner, D. Uptake and metabolism of 2,4,6-trinitrotoluene in higher plants. *Environ. Sci. & Pollut. Res.,* 229 (1994), Pennington, J. C. (ed Army Engineering Waterways Experiment Station) (Vicksburg, Miss., USA, 1988), and Schneider, K., Oltmanns, J., Radenberg, T., Schneider, T. & Mundegar, D. Uptake of nitroaromatic compounds in plants. *Environ. Sci. & Pollut. Res.* 3, 135-138 (1996), each of which is incorporated by reference in its entirety.

Recently, several studies have reported the introduction of remediation or biochemical detection abilities onto plants by using genetic engineering approaches. Nagata and coworkers demonstrated the use of genetically engineered transgenic tobacco for phytoremediation of low levels of mercury contamination. See, Nagata, T., Nakumura, A., Akizawa, T. & Panhou, H. Genetic engineering of transgenic tobacco for enhanced uptake and bioaccumulation of mercury. *Biol Pharm Bull* 32, 1491-1495 (2009), which is incorporated by reference in its entirety. This was achieved via enhanced uptake and bioaccumulation of mercury by the transgenic tobacco plant. In recent years, Medford and coworkers have also genetically modified tobacco plants such that a de-greening response is elicited upon detection of trinitrotoluene. See, Antunes, M. et al. Programmable ligand detection system in plants through a synthetic signal transduction pathway. *PloS ONE* 6 (2011), which is incorporated by reference in its entirety.

Genetic modification allows for easy scaling via reproduction, however, this potentially introduces difficulty in population control. A small number of plant species allow facile modification in this way, including Tobacco and *Arabidopsis*, but not those generally adapted to specific environments as one can achieve with a wild type modification. Lastly, while genetic engineering can introduce non-native communication channels such as degreening, wilting or fluorescent protein expression, such methods cannot interface to a wide range of human technologies, such as infrared telecommunications, or electronic signaling in obvious ways. Furthermore, these genetic responses to the environment span over the course of days or weeks while infrared communications via nanoparticles are in real-time.

Disclosed herein is a sensor using a living plant that can function as self-powered auto-samplers and preconcentrators of an analyte within ambient groundwater, detectors of the analyte contained therein. For example, a pair of near infrared (IR) fluorescent sensors embedded within a plant can be used as detectors of the nitroaromatic molecules, with the first IR channel engineered through CoPhMoRe to recognize analyte via IR fluorescent emission and the second IR channel including a functionalized nanostructure that acts as an invariant reference signal. A pair of near infrared (IR) fluorescent sensors can be embedded within a cell, an organelle, or a tissue of a plant, where a nanoparticle can enter, such as leaf mesophyll cells and stomata guard cells, and localize near the organelles, chloroplasts and mitochondria.

Also disclosed herein is a graphene-leaf hybrid material that can regulate the transpiration rate, potentially enabling sensing as well as control of analyte residence times. These results demonstrate how whole wild-type living plants can be engineered into new functional materials using specifically designed nanomaterials.

A nitroaromatic detecting wild-type spinach plant using a nanobionic approach can respond to picric acid, which is commonly found in explosives. Living spinach plants (*Spinacia oleracea*) can function as self-powered auto-samplers and preconcentrators of nitroaromatics within ambient groundwater, detectors of the nitroaromatic molecules contained therein, and infrared communication platforms that can send this information to a user's cell phone. A pair of near infrared fluorescent sensors embedded within the mesophyll of the plant leaf can be used, with one engineered through Corona Phase Molecular Recognition (CoPhMoRe) using the peptide Bombolitin II to recognize nitro-aromatics via an infrared (IR) fluorescent emission. The second IR channel can be a polyvinyl alcohol (PVA) functionalized SWCNT that acts as an invariant reference signal. The pair is infiltrated into the leaf tissues via stomata pores in the leaf lamina. As the nitroaromatics in solution are transported up the roots and stem into the leaf tissues, they come into contact with the embedded SWCNT sensors, inducing changes in the intensity of SWCNT emission, with a response rate characterized by $k_{root}$=0.016 (mM·min)$^{-1}$. The real-time monitoring of embedded SWCNT sensors also allows residence times in the roots, stems and leaves to be estimated, which is calculated to be 2-5 min, 3-6 min and 5-10 min respectively.

Corona Phase Molecular Recognition (CoPhMoRe) is a generic molecular recognition scheme using a nanoparticle surface to template a heteropolymer. An adsorbed phase of a surfactant or a polymer on a nanoparticle, called the corona, and normally selected from a library of such molecules, is necessarily constrained and structured by the molecular interactions with the nanoparticle surface. CoPhMoRe is achieved when a heteropolymer-nanoparticle hybrid selectively binds a target analyte owing to the structure adopted by the polymer when folded onto the particle surface. In practice, a CoPhMoRe screen of a heteropolymer or surfactant library is accelerated if the underlying nanoparticle has an optical response to the molecular binding event, allowing for high throughput detection of the selective phase.

Previous in vitro work demonstrated that a class of peptides from the bombolitin family allows near-infrared fluorescent SWCNTs to transduce specific changes in their conformation. See, Heller, D. A., et al. Peptide secondary structure modulates single-walled carbon nanotube fluorescence as a chaperone sensor for nitroaromatics. *Proc Natl*

Acad Sci 108, 8544-8549 (2011), which is incorporated by reference in its entirety. In response to the binding of specific nitroaromatic compounds, such peptide-nanotube complexes can form a virtual "chaperone sensor", which reports modulation of the peptide secondary structure via attenuation or spectra shifts in SWCNT near-infrared photoluminescence. The SWCNTs fluorescence in the nIR region overlaps with the tissue transparency window and benefits from reduced autofluorescence, making SWCNT-based sensors ideal for plant in vivo applications. See, Oliveira, S. F. et al. Protein functionalized carbon nanomaterials for biomedical applications. *Carbon* 95, 767-779 (2015), Iverson, N. M. et al. Quantitative Tissue Spectroscopy of Near Infrared Fluorescent Nanosensor Implants. *Journal of Biomedical Nanotechnology* 12, 1035-1047 (2016), and Bisker, G., Iverson, N. M., Ahn, J. & Strano, M. S. A Pharmacokinetic Model of a Tissue Implantable Insulin Sensor. *Advanced Healthcare Materials* 4, 87-97 (2015), each of which is incorporated by reference in its entirety. The Bombolitin-SWCNT sensors are first embedded into the leaf of a *Spinacia oleracea* plant via pressure infiltration. See, Giraldo, J. P., Laundry, M. P., Faltermeier, S. M., McNicholas, T. P., Iverson, N. M., Boghossian, A. A, Rueul, N. F., Hilmer, A. J., Sen, F., Brew, J. A., Strano, M. S. Plant nanobionics approach to augment photosyesis and biochemical sensing. *Nat Mater* 13, doi:10.1038/nmat389010.1038/NMAT3890 (2014), which is incorporated by reference in its entirety. Picric acid is then delivered in one of two ways—either via direct uptake through the leaf surface, or via root uptake. In both cases, the in vivo Bombolitin-SWCNT intensity was observed to quench in response to uptake of picric acid by the plant. This information is then communicated wirelessly via nIR signals to a standoff detector and the spatial resolution of the quenching dynamics was used to provide insights into the transport of nitroaromatics in the leaf. It was further demonstrated that a miniaturized and portable stand-off detector setup based on the RaspberryPi® can also be used for nitroaromatic detection. Such a standoff system would enable the monitoring of a wide area with few sensors and at safe distances. See, Johansson, I., Wallin, S., Nordberg, M., H., O. & Pettersson, A. Near real-time standoff detection of explosives in a realistic outdoor environment at 55 m distance. *Propellants Explos. Pyrotech* 34, 297-306 (2009), which is incorporated by reference in its entirety. The in vivo usage of these chaperone sensors in wild type plants coupled with low cost, fast and portable stand-off systems enables a nitroaromatic detecting plant that is capable of the autosampling of chemical analytes in the environment and thereafter infrared communication to the end-user. The modification of the wild-type plant in this way allows the fluorescent nanosensor and reference signal to detect and report the presence of nitroaromatic molecules in leaf mesophyll where they are necessarily pre-concentrated, being less volatile than the aqueous solvent.

Developing stand-off devices for detecting the spectral shift would allow for this technology to become widespread. For example, a FLIR SC6200 nIR camera can be used to accomplish standoff detection of SWNT nIR emission. This approach can be used to image semiconducting SWNT and SWNT-based sensors within plants from a distance of several meters and even from a satellite.

The use of nanoparticles to create nanobionic plants with the ability to serve as real time nitroaromatic detectors and thereafter, report the detection of picric acid via attenuation of nIR fluorescence in functionalized leaves. This is performed in a standoff manner and can be achieved through inexpensive equipment, such as the RaspberryPi® and CCD camera. This nanobionic approach potentially enables a wide variety of wild type plants to be used for infrared communication and the wide-area and real time monitoring of the environment.

The 10-15 μm stomatal pores on the both adaxial and abaxial sides of a leaf are highly permeable to nanoparticles (FIG. 1A), but once in the mesophyll, the nanoparticle size and surface charge restrict further localization. See, Giraldo, J. P. et al. Plant nanobionics approach to augment photosynthesis and biochemical sensing. *Nat Mater* 13, 400-408, doi:10.1038/nmat3890 (2014), and Eichert, T., Kurtz, A., Steiner, U. & Goldbach, H. E. Size exclusion limits and lateral heterogeneity of the stomatal foliar uptake pathway for aqueous solutes and water-suspended nanoparticles. *Physiol Plantarum* 134, 151-160, doi:10.1111/j.1399-3054.2008.01135.x (2008), each of which is incorporated by reference in its entirety. Silica nanoparticles below 10 nm in dimension can enter leaf mesophyll cells and stomata guard cells, and localize near the organelles, chloroplasts and mitochondria, where ATP generation is highest. The stomata open when the guard cells increase in volume, which can happen in minutes and requires rapid and massive transport of solute across the guard cell membrane. See, Schroeder, J. I., Raschke, K. & Neher, E. Voltage Dependence of K+ Channels in Guard-Cell Protoplasts. *Proc Natl Acad Sci USA* 84, 4108-4112, doi:DOI 10.1073/pnas.84.12.4108 (1987), which is incorporated by reference in its entirety. The uneven thickness of the stomata guard cell wall and the solute transport through the cell membrane may promote SNP of small enough size to localize within stomata guard cells. See, Evert, R. F. Epidermis. *Esaus Pflanzenanatomie: Meristeme, Zellen Und Gewebe Der Pflanzen Ihre Struktur, Funktion Und Entwicklung*, 193-232, doi:Book_Doi 10.1515/9783110211320 (2009), which is incorporated by reference in its entirety.

One advantage of this nanobionic approach is that the function of specific regions within tissues can be targeted, which is demonstrated by using leaf laminar infiltration of nanoparticles (LIN) through stomatal pores employed previously. See Giraldo, J. P. et al. Plant nanobionics approach to augment photosynthesis and biochemical sensing. *Nat Mater* 13, 400-408, doi:10.1038/nmat3890 (2014), which is incorporated by reference in its entirety. Fluorescence confocal micrographs of spinach leaves infiltrated by LIN showed that both leaf epidermal cell and leaf mesophyll cell regions showed similar nanoparticles distribution. Some nanoparticles can be located in guard cells, but mostly in air spaces surrounding sponge mesophyll cells. Cell membranes are intact. The ability to easily modify wild-type plants is a notable advantage of this nanobionic approach.

Another advantage of such an approach is that it is possible to shift the light emission to other wavelengths using resonant energy transfer to a semiconductor nanocrystal. The emission can be further enhanced after the addition of ATP, however nIR emission is clearly detectable using the plant's own ATP exclusively. This demonstration illustrates the potential for ambient IR communications from a plant system, with future work to address control of modulation and multiplexing for more complex communications to external electronic devices.

The disclosed nanobionic light emitting plants with record levels of both brightness and luminescent lifetime, tissue specific patterning and wavelength modulation through resonant energy transfer open possibilities towards useful tools to create plants with non-native functions, photonic sources for indirect lighting and nIR communications, as well as to contribute to the fundamental study of plant biology in a variety of wild-type plants.

As used herein, the term "nanoparticle" refers to articles having at least one cross-sectional dimension of less than about 1 micron. A nanoparticle can also be referred to as a "nanostructure." A nanoparticle can have at least one cross-sectional dimension of less than about 500 nm, less than about 250 nm, less than about 100 nm, less than about 75 nm, less than about 50 nm, less than about 25 nm, less than about 10 nm, less than 5 nm, or, in some cases, less than about 1 nm. Examples of nanoparticle include nanotubes (e.g., carbon nanotubes), nanowires (e.g., carbon nanowires), nanosheets, graphene, and quantum dots, among others. In some embodiments, the nanoparticle can include a fused network of atomic rings, the atomic rings comprising a plurality of double bonds.

A nanoparticle can be a photoluminescent nanoparticle. A "photoluminescent nanoparticle," as used herein, refers to a class of nanoparticles that are capable of exhibiting photoluminescence. In some cases, photoluminescent nanoparticles can exhibit fluorescence. In some instances, photoluminescent nanoparticles exhibit phosphorescence. Examples of photoluminescent nanoparticles suitable for use include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, and graphene, among others.

A variety of nanoparticles can be used. Sometimes a nanoparticle can be a carbon-based nanoparticle. As used herein, a "carbon-based nanoparticle" can include a fused network of aromatic rings wherein the nanoparticle includes primarily carbon atoms. In some instances, a nanoparticle can have a cylindrical, pseudo-cylindrical, or horn shape. A carbon-based nanoparticle can include a fused network of at least about 10, at least about 50, at least about 100, at least about 1000, at least about 10,000, or, in some cases, at least about 100,000 aromatic rings. A carbon-based nanoparticle may be substantially planar or substantially non-planar, or may include a planar or non-planar portion. A carbon-based nanoparticle may optionally include a border at which the fused network terminates. For example, a sheet of graphene includes a planar carbon-containing molecule including a border at which the fused network terminates, while a carbon nanotube includes a non-planar carbon-based nanoparticle with borders at either end. In some cases, the border may be substituted with hydrogen atoms. In some cases, the border may be substituted with groups comprising oxygen atoms (e.g., hydroxyl).

In some embodiments, a nanoparticle can include or be a nanotube. The term "nanotube" is given its ordinary meaning in the art and can refer to a substantially cylindrical molecule or nanoparticle including a fused network of primarily six-membered rings (e.g., six-membered aromatic rings). In some cases, a nanotube can resemble a sheet of graphite formed into a seamless cylindrical structure. It should be understood that a nanotube may also include rings or lattice structures other than six-membered rings. Typically, at least one end of the nanotube may be capped, i.e., with a curved or non-planar aromatic group. A nanotube may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may include a carbon nanotube. The term "carbon nanotube" can refer to a nanotube including primarily carbon atoms. Examples of carbon nanotubes can include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, a carbon nanotube can be a single-walled carbon nanotube. In some cases, a carbon nanotube can be a multi-walled carbon nanotube (e.g., a double-walled carbon nanotube).

In some embodiments, a nanoparticle can include non-carbon nanoparticles. In certain embodiments, a nanoparticle can be a metallic nanoparticle. In some instances, the nanoparticle can include palladium, gold, or other noble metals.

In some embodiments, a nanoparticle can be a non-carbon nanotube. Non-carbon nanotubes may be of any of the shapes and dimensions outlined above with respect to carbon nanotubes. A non-carbon nanotube material may be selected from polymer, ceramic, metal and other suitable materials. For example, a non-carbon nanotube may include a metal such as Co, Fe, Ni, Mo, Cu, Au, Ag, Pt, Pd, Al, Zn, or alloys of these metals, among others. In some instances, a non-carbon nanotube may be formed of a semi-conductor such as, for example, Si. In some cases, a non-carbon nanotube may include a Group II-VI nanotube, wherein Group II includes Zn, Cd, and Hg, and Group VI includes O, S, Se, Te, and Po. In some embodiments, a non-carbon nanotube may include a Group III-V nanotube, wherein Group III includes B, Al, Ga, In, and Tl, and Group V includes N, P, As, Sb, and Bi. As a specific example, a non-carbon nanotube may include a boron-nitride nanotube. In other embodiments, the nanoparticle can be a ceramic, for example, a metal oxide, metal nitride, metal boride, metal phosphide, or metal carbide. In this example, the metal can be any metal, including Group I metal, Group II metal, Group III metal, Group IV metal, transition metal, lanthanide metal or actinide metal. For example, the ceramic can include one or more of metal, for example, Li, Na, K, Rb, Cs, Be, Mg, Ca, Sr, Ba, Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os, Co, Rh, Ir, Ni, Pd, Pt, Cu, Ag, Su, Zn, Cd, Hg, Al, Ga, In, Tl, Si, Ge, Sn, Pb or Bi.

In some embodiments, a nanotube may include both carbon and another material. For example, in some cases, a multi-walled nanotube may include at least one carbon-based wall (e.g., a conventional graphene sheet joined along a vector) and at least one non-carbon wall (e.g., a wall comprising a metal, silicon, boron nitride, etc.). In some embodiments, the carbon-based wall may surround at least one non-carbon wall. In some instances, a non-carbon wall may surround at least one carbon-based wall.

The term "quantum dot" is given its normal meaning in the art and can refer to semi-conducting nanoparticles that exhibit quantum confinement effects. Generally, energy (e.g., light) incident upon a quantum dot can excite the quantum dot to an excited state, after which, the quantum dot can emit energy corresponding to the energy band gap between its excited state and its ground state. Examples of materials from which quantum dots can be made include PbS, PbSe, CdS, CdSe, ZnS, and ZnSe, among others.

A photoluminescent nanoparticle can be, in some cases, substantially free of dopants, impurities, or other non-nanoparticle atoms. For example, in some embodiments, a nanoparticle can include a carbon nanoparticle that is substantially free of dopants. As a specific example, in some embodiments, a nanoparticle can include single-walled carbon nanotube that contains only aromatic rings (each of which contains only carbon atoms) within the shell portion of the nanotube. In other words, a nanoparticle can consist essentially of a single material, for example, carbon.

In some embodiments, a photoluminescent nanoparticle may emit radiation within a desired range of wavelengths. For example, in some cases, a photoluminescent nanoparticle may emit radiation with a wavelength between about 750 nm and about 1600 nm, or between about 900 nm and about 1400 nm (e.g., in the near-infrared range of wavelengths). In some embodiments, a photoluminescent nanoparticle may emit radiation with a wavelength within the visible range of the spectrum (e.g., between about 400 nm and about 700 nm).

In some embodiments, a photoluminescent nanoparticle may be substantially free of covalent bonds with other entities (e.g., other nanoparticles, a current collector, the surface of a container, a polymer, an analyte, etc.). The absence of covalent bonding between a photoluminescent nanoparticle and another entity may, for example, preserve the photoluminescent character of the nanoparticle. In some cases, single-walled carbon nanotubes or other photoluminescent nanoparticles may exhibit modified or substantially no fluorescence upon forming a covalent bond with another entity (e.g., another nanoparticle, a current collector, a surface of a container, and the like).

In some embodiments, a nanoparticle can include cerium oxide. A nanoparticle including cerium oxide can be referred to as nanoceria. A nanoparticle can be cerium oxide. A nanoparticle can also be conjugated to at least one cerium oxide nanoparticle. Conjugation can be direct or indirect. Conjugation can also be through a covalent bond, ionic bond or van der Waals interaction. A nanoparticle can be cross-linked with at least one cerium oxide nanoparticle, more specifically, cross-linked using via carbodiimide chemistry. In one example, a carbodiimide agent N-ethyl-N'-(3-dimethylaminopropyl) carbodiimide hydrochloride (EDC) can be used.

A nanoparticle can be strongly cationic or anionic. Strongly cationic or anionic can mean that the nanoparticle (or other element) has a high magnitude of the zeta potential. For example, the nanoparticle can have a zeta potential of less than −10 mV or greater than 10 mV. In preferred embodiments, the nanoparticle can have a zeta potential of less than −20 mV or greater than 20 mV, a zeta potential of less than −30 mV or greater than 30 mV, or a zeta potential of less than −40 mV or greater than 40 mV.

A nanoparticle can include a coating or be suspended in a coating with a high magnitude of the zeta potential. A coating can be a polymer. A variety of polymers may be used in association with the embodiments described herein. In some cases, the polymer may be a polypeptide. In some embodiments, the length and/or weight of the polypeptide may fall within a specific range. For example, the polypeptide may include, in some embodiments, between about 5 and about 50, or between about 5 and about 30 amino acid residues. In some cases, the polypeptide may have a molecular weight of between about 400 g/mol and about 10,000 g/mol, or between about 400 g/mol and about 600 g/mol. Examples of protein polymers can include glucose oxidase, bovine serum albumin and alcohol dehydrogenase.

The polymer may include Bombolitin. In some embodiments, the polymer may include a synthetic polymer (e.g., polyvinyl alcohol, poly(acrylic acid), poly(ethylene oxide), poly(vinyl pyrrolidinone), poly(allyl amine), poly(2-vinylpyridine), poly(maleic acid), and the like), in some embodiments.

In some embodiments, the polymer may include an oligonucleotide. The oligonucleotide can be, in some cases, a single-stranded DNA oligonucleotide. The single-stranded DNA oligonucleotide can, in some cases, include a majority (>50%) A or T nucleobases. In some embodiments, single-stranded DNA oligonucleotide can include more than 75%, more than 80%, more than 90%, or more than 95% A or T nucleobases. In some embodiments, the single-stranded DNA oligonucleotide can include a repeat of A and T. For example, a oligonucleotide can be, in some cases, at least 5, at least 10, at least 15, between 5 and 25, between 5 and 15, or between 5 and 10 repeating units, in succession, of (GT) or (AT). Repeating units can include at least 2 nucleobases, at least 3 nucleobases, at least 4 nucleobases, at least 5 nucleotides long. The nucleobases described herein are given their standard one-letter abbreviations: cytosine (C), guanine (G), adenine (A), and thymine (T).

In some embodiments, the polymer can include a polysaccharide such as, for example, dextran, pectin, hyaluronic acid, hydroxyethylcellulose, amylose, chitin, or cellulose.

In preferred embodiments, the interaction between a polymer and a nanoparticle can be non-covalent (e.g., via van der Waals interactions); however, a polymer can covalently bond with a nanoparticle. In some embodiments, the polymer may be capable of participating in a pi-pi interaction with the nanostructure. A pi-pi interaction (a.k.a., "pi-pi stacking") is a phenomenon known to those of ordinary skill in the art, and generally refers to a stacked arrangement of molecules adopted due to interatomic interactions. Pi-pi interactions can occur, for example, between two aromatic molecules. If the polymer includes relatively large groups, pi-pi interaction can be reduced or eliminated due to steric hindrance. Hence, in certain embodiments, the polymer may be selected or altered such that steric hindrance does not inhibit or prevent pi-pi interactions. One of ordinary skill in the art can determine whether a polymer is capable or participating in pi-pi interactions with a nanostructure.

The polymer may be strongly cationic or anionic, meaning that the polymer has a high magnitude of the zeta potential. For example, the polymer can have a zeta potential of less than −10 mV or greater than 10 mV, less than −20 mV or greater than 20 mV, less than −30 mV or greater than 30 mV, or less than −40 mV or greater than 40 mV.

A nanoparticle can be contained within a mesophyll or stomata guard cells, as demonstrated more fully herein. A nanoparticle can traverse and/or localize within the outer membrane layer (i.e., lipid bilayer). The process can be complete and/or irreversible. Because other organelles include an outer membrane layer (i.e., lipid bilayer), a nanoparticle can be contained within other organelles. For example, other organelles that a nanoparticle can be introduced into can include a nucleus, endoplasmic reticulum, Golgi apparatus, chloroplast, chromoplast, gerontoplast, leucoplast, lysosome, peroxisome, glyoxysome, endosome, mitochondria or vacuole.

Thylakoids are a membrane-bound compartment inside a chloroplast. Cyanobacteria can also include thylakoids. In some embodiments, a nanoparticle can be associated with a thylakoid membrane within a chloroplast, cyanobacteria or other photocatalytic cell or organelle.

A nanoparticle can be contained within a photocatalytic unit, most preferably, including an outer lipid membrane (i.e., lipid bilayer). A photocatalytic unit can be a structure capable of performing photosynthesis or photocatalysis, preferably a cell or an organelle capable of performing photosynthesis or photocatalysis. For example, a photocatalytic unit can be a chloroplast, a cyanobacteria, or a bacterial species selected from the group consisting of *Chlorobiacea* spp., a *Chromaticacea* spp. and a *Rhodospirillacae* spp.

An organelle can be part of a cell, a cell can be part of a tissue, and a tissue can be part of an organism. For example, a nanoparticle can be contained within a cell of a leaf of a plant. More to the point, a cell can be intact. In other words, the organelle may not be an isolated organelle, but rather, the organelle can be contained within the outer lipid membrane of a cell.

A nanoparticle that is independent of an organelle or cell can be free of lipids. An outer lipid membrane can enclose or encompass an organelle or cell. As the nanoparticle traverses the outer lipid membrane of an organelle or cell, lipids from the outer lipid membrane can associate or coat the nanoparticle. As a result, a nanoparticle inside the outer lipid membrane of an organelle or cell can be associated with or coated with lipids that originated in the organelle or cell.

Transport of a nanoparticle into an organelle or a cell can be an active process. In some cases, transport across the outer lipid membrane can be dependent on the pressure, temperature or light conditions.

Transport of a nanoparticle into an organelle or a cell can be a passive process. In some cases, transport across the outer lipid membrane can be independent of the pressure, temperature or light conditions.

Embedding a nanoparticle within an organelle or cell can be useful for monitoring the activity of the organelle or cell. For example, a nanoparticle, preferably a photoluminescent nanoparticle, can be introduced into a organelle or a cell. Measurements of the photoluminescence of a photoluminescent nanoparticle can provide information regarding a stimulus within an organelle or cell. Measurements of the photoluminescence of a photoluminescent nanoparticle can be taken at a plurality of time points. A change in the photoluminescence emission between a first time point and a second time point can indicate a change in a stimulus within the organelle or cell.

In some embodiments, a change in the photoluminescence emission can include a change in the photoluminescence intensity, a change in an emission peak width, a change in an emission peak wavelength, a Raman shift, or combination thereof. One of ordinary skill in the art would be capable of calculating the overall intensity by, for example, taking the sum of the intensities of the emissions over a range of wavelengths emitted by a nanoparticle. In some cases, a nanoparticle may have a first overall intensity, and a second, lower overall intensity when a stimulus changes within the organelle or cell. In some cases, a nanoparticle may emit a first emission of a first overall intensity, and a second emission of a second overall intensity that is different from the first overall intensity (e.g., larger, smaller) when a stimulus changes within the organelle or cell.

A nanoparticle may, in some cases, emit an emission of radiation with one or more distinguishable peaks. One of ordinary skill in the art would understand a peak to refer to a local maximum in the intensity of the electromagnetic radiation, for example, when viewed as a plot of intensity as a function of wavelength. In some embodiments, a nanoparticle may emit electromagnetic radiation with a specific set of peaks. In some cases, a change in a stimulus may cause the nanoparticle to emit electromagnetic radiation including one or more peaks such that the peaks (e.g., the frequencies of the peaks, the intensity of the peaks) may be distinguishable from one or more peaks prior to the change in stimulus. In some cases, the change in a stimulus may cause the nanoparticle to emit electromagnetic radiation comprising one or more peaks such that peaks (e.g., the frequencies of the peaks, the intensity of the peaks) are distinguishable from the one or more peaks observed prior to the change in the stimulus. When the stimulus is the concentration of an analyte, the frequencies and/or intensities of the peaks may, in some instances, allow one to determine the analyte interacting with the nanoparticle by, for example, producing a signature that is unique to a particular analyte that is interacting with the nanoparticle. Determination of a specific analyte can be accomplished, for example, by comparing the properties of the peaks emitted in the presence of the analyte to a set of data (e.g., a library of peak data for a predetermined list of analytes).

A stimulus can include the pH of the organelle or cell. A change in the pH can be an increase or decrease in the pH.

A stimulus can include a modification of an analyte. For example, an analyte may be oxidized or reduced. In other examples, an analyte can be ionized. In another example, an analyte can include an ether, ester, acyl, or disulfide or other derivative.

A stimulus can include the concentration of an analyte. An analyte can include a reactive oxygen species, for example, hydrogen peroxide, superoxide, nitric oxide, or a peroxidase. Alternatively, an analyte can be carbon dioxide, adenosine triphosphate (ATP), nicotinamide adenine dinucleotide phosphate ($NADP^+$ or NADPH), oxygen, or nitroaromatics. In some instances, the concentration of the analyte may be relatively low (e.g., less than about 100 micromolar, less than about 10 micromolar, less than about 1 micromolar, less than about 100 nanomolar, less than about 10 nanomolar, less than about 1 nanomolar, or about a single molecule of the analyte). In some cases, the concentration of an analyte may be zero, indicating that no analyte is present.

Functionalized nanotubes can be useful in many areas. In one embodiment, nanotubes can be functionalized in different ways to serve as sensors for harmful compounds. To detect explosives, bombolitin-functionalized nanotubes can be infused into the leaves of the plant. Bombolitin is a unique peptide which allows for recognition of nitroaromatics, the key compounds in many explosives. Therefore, a plant with bombolitin-functionalized nanoutbes can recognize the nitroaromatics from explosives. Using stand-off devices for detecting the spectral shift, semiconducting SWNT and SWNT-based sensors within plants can be imaged from a distance of several meters to hundreds of metters, for example, from 3-10 meters, 10-40 meters, 40-100 meters, 100-500 meters, or 500-1000 meters, and even from a satellite.

Figure 6A:
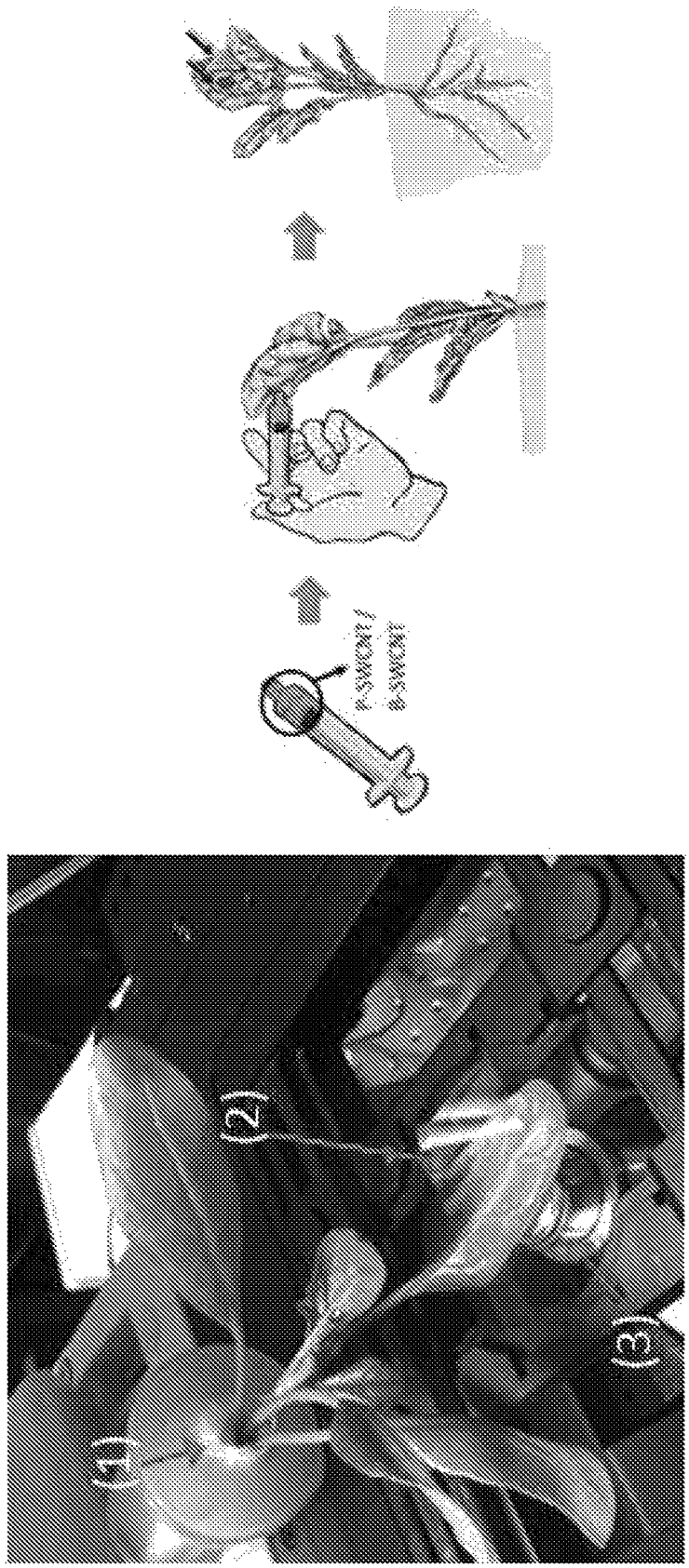
FIGS. 6A-6B show changes in NIR fluorescence spectra of Bombolitin-SWCNT and PVA-SWCNT inside leaves of living plants in response to picric acid.
Figure 6B:
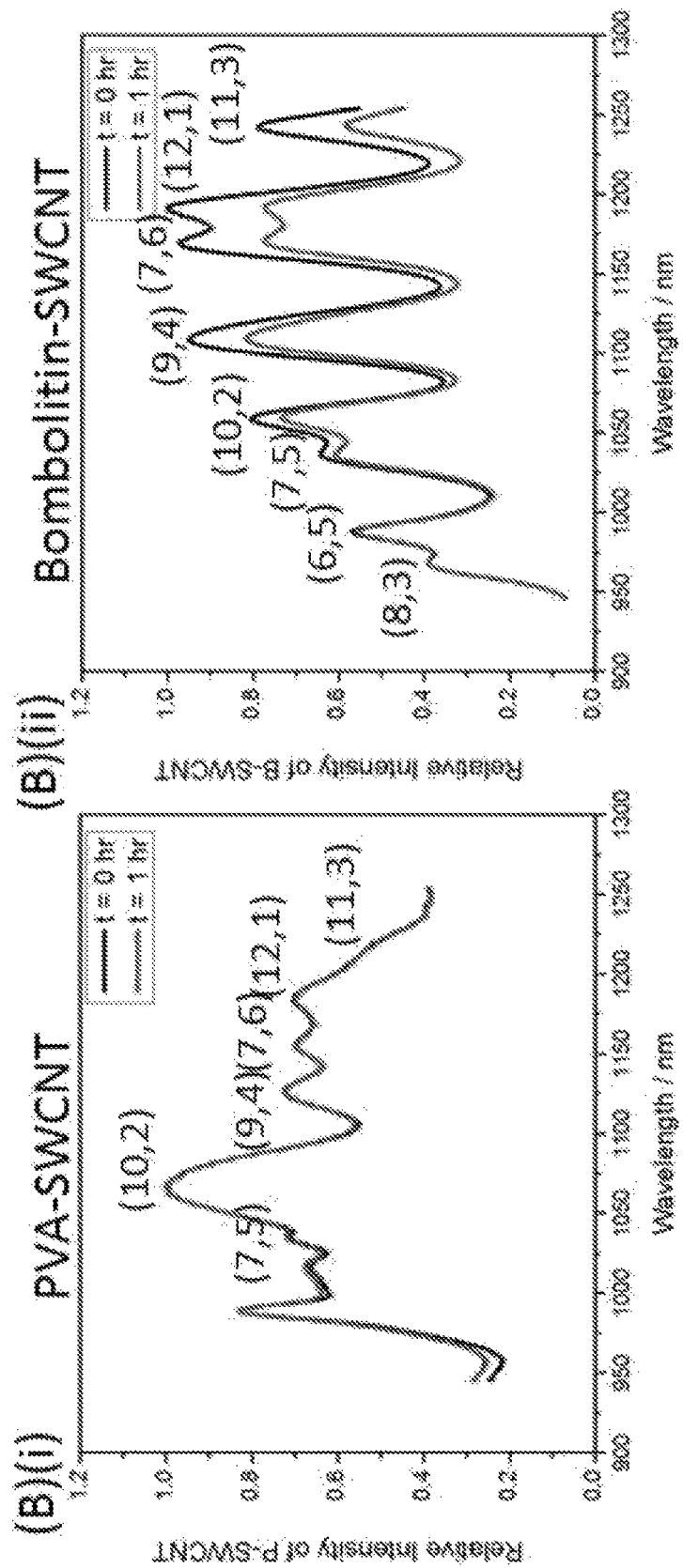

Nanotubes can be functionalized in different ways to serve as sensors for harmful compounds. Bombolitin is a unique peptide which allows for recognition of nitroaromatics, the key compounds in many explosives. See, Heller, D., Pratt, G. & Zhang, J., 2011. Peptide secondary structure modulates single-walled carbon nanotube fluorescence as a chaperone sensor for nitroaromatics. *Proceedings of the National Academy of Sciences U.S.A.*, 108(21), pp. 8544-8549, which is incorporated by reference in its entirety. Using bombolitin to coat carbon nanotubes results in stronger recognition and easily differentiable spectral shifts. The functionalization of the carbon nanotube surface can result in completely unique sites for recognition, resolvable at the single-molecule level. Airborne nitroaromatic molecules can enter a plant system alongside carbon dioxide and water vapor from the air. Any bombolitin-functionalized nanotubes infused into the leaves of the plant would recognize the nitroaromatics and would display a spectral shift upon change in the bombolitin's secondary structure. The modified plant can effectively act as a nitroaromatic-sensing plant. Such nanobionic plants do not rely upon genetic modification, and therefore the nitroaromatics-sensing function can be given to almost any plant. This technology can be applied to airports, hospitals, and other areas where security is a major concern. Indoor plants used for their aesthetic value in these locations can double as nitroaromatics sensors.

A light emitting compound immobilized on nanoparticles can be introduced to a green plant to make an autoluminescent plant. In one embodiment, co-immobilization of luciferase and luciferin on mesoporous silica nanoparticles can make autoluminescent plants without genetic modification. Immobilizing luciferase on silica nanoparticles with ATP in plant leaves can make the luminescence reactions to glow for longer time durations compared to free luciferase in a leaf.

The interface between plant organelles and non-biological nanoparticles has the potential to impart the former with new and enhanced functions. For example, this nanobionic approach can yield chloroplasts that possess enhanced photosynthetic activity both ex vivo and in vivo, are more stable to reactive oxygen species ex vivo, and allow real time information exchange via embedded nanosensors for free radicals in plants. Accordingly, there is a need for nanoparticles that can interface with organelles, specifically, plant organelles ex vivo and in vivo to enable novel or enhanced functions. Similarly, there is a need for nanoparticles that can interface with intact photosynthetic organisms or intact cells of photosynthetic organisms ex vivo and in vivo to enable novel or enhanced functions. For example, the assembly of nanoparticle complexes within chloroplast photosynthetic machinery has the potential to enhance solar energy conversion through augmented light reactions of photosynthesis and ROS scavenging while imparting novel sensing capabilities to living plants.

Nanobionic methods interfacing low dimensional materials with plants can enable non-native functionalities to be introduced to wild-type plants relatively rapidly and easily. For instance, the stomatal behavior of wild-type plants can be regulated via the addition of a water-impermeable barrier of a 2D material such as a graphene monolayer to the external leaf surface such that the effective stomatal aperture (FIG. 8A) is reduced to essentially zero. The transfer of a graphene-poly(methyl methacrylate) (PMMA) monolayer as a water-impermeable barrier to the abaxial side of the spinach leaf surface (FIG. 8B) maintains stomatal response to light. Strikingly, while bare stomata are completely closed in the dark, the introduction of a graphene-PMMA layer results in stomata partially opening under dark conditions (FIGS. 9A-9B and 10A-10E). Under illumination however, stomatal aperture function was unaffected by the addition of the graphene layer, opening up the potential to use these two components simultaneously. The barrier can function as a transpiration regulator that can increase residence times of volatile analytes within the plant mesophyll by suppressing local evaporation around the sensor, demonstrating the large variety of functionalities that may result from nanobionic methods interfacing 2D materials with living plants.

The use of nanoparticles to create nanobionic plant enabled sensors that detect nitroaromatics in real time and thereafter the detection of picric acid via attenuation of nIR fluorescence in functionalized leaves can be performed in a standoff manner and can be achieved through inexpensive equipment, such as the Raspberry Pi®. This platform is generalizable to other physiologically relevant molecules, such as dopamine. The nanobionic approach creates a new class of functional plant nanomaterial hybrids that opens the door to the use of wild type plants for infrared communication in wide-areas, and real time monitoring of environments such as cities, crop fields, high security facilities, and homes.

Detection of Picric Via Root Uptake Using Nanobionic *Spinacia oleracea* Plant Nanobionic Functionalization of *Spinacia oleracea*

The functionalized nitroaromatic detecting plant was prepared as follows. Spinach plants (3 weeks old) were first transplanted into a small beaker with 10 mM KCl buffer to maintain root osmolarity. The roots were gently wrapped with cheese cloth. The plants were converted into detectors of nitroaromatics via infiltration through the leaf lamina with single walled carbon nanotubes (SWCNT) coated in PVA and Bombolitin. Briefly, P-SWCNT (P-SWCNT) and Bombolitin-SWCNT (B-SWCNT) (see Examples for SWCNT preparation) were infiltrated using a needle-less syringe into two regions of a single leaf's lamina separated by the mid vein (FIG. 1A), where they get embedded into the parenchyma tissues of the leaf lamina (co-localization observed in FIG. 1B). See, Giraldo, J. P., Laundry, M. P., Faltermeier, S. M., McNicholas, T. P., Iverson, N. M., Boghossian, A. A, Rueul, N. F., Hilmer, A. J., Sen, F., Brew, J. A., Strano, M. S. Plant nanobionics approach to augment photosythesis and biochemical sensing. *Nat Mater* 13, (2014), which is incorporated by reference in its entirety. It was estimated that approximately $1.6\times10^{-7}$ g or $1.9\times10^{10}$ of B-SWCNTs and P-SWCNTs were infiltrated into the leaf. As leaves transpire, water and other analytes are drawn up by the roots into the stem and towards leaf tissues via the plant vasculature. Leaves are infiltrated with B-SWCNTs (active sensor) and P-SWCNTs (reference sensor) via the abaxial surface on each side of the leaf midrib. SWCNTs have been previously shown to penetrate cell walls and membranes of tobacco cell cultures (see, Liu, Q. et al. Carbon nanotubes as molecular transporters for walled plant cells. *Nano Lett.* 9, 1007-1010 (2009), which is incorporated by reference in its entirety), and MWCNTs have recently been reported to be able to translocate within the plant vasculature. See, Chen, G. et al. Carbon nanotubes act as contaminant carriers and translocate within plants. *Scientific Reports* 5 (2015), which is incorporated by reference in its entirety. Picric acid (2,4,6-trinitrophenol), which is commonly used in explosives (see, Chen, P., Zhang, L., Zhu, S. & Cheng, G. A comparative theoretical study of picric acid and its cocrystals. *Crystals* 5, 346-354 (2015), which is incorporated by reference in its entirety) was used as a model nitroaromatic compound for this study. The nIR fluorescence signal of P-SWCNT is invariant to picric acid, enabling it to function as a reference sensor in the plant (FIG. 5). In FIG. 5, The spectra of 200 uL suspensions of P-SWCNT and B-SWCNT was recorded before and after 10 min of adding 10 uL of picric acid 0.4 mM. Laser excitation 785 nm at 0.90 mW. The nIR fluorescence intensity of B-SWCNT quenches in response to picric acid, and enables its function as an active sensor (FIG. 5). As water and other analytes are transported up the plant via the roots and plant vasculature, they eventually reach the leaf tissues and come into contact with the embedded sensors (FIG. 1A). The presence of picric acid is conveyed in the form of intensity attenuation of B-SWCNT fluorescence (IR Channel 2, FIG. 1A), and is monitored by a detector. The ability of the plant to function as a groundwater sampler of picric acid was first confirmed through the use of nIR microscopy (FIGS. 6A-6B), before a standoff detection set up was developed for far-field monitoring of nitroaromatics. In FIG. 6A, the functionalized leaf was gently held in place on glass slides and exposed to 785 nm laser excitation on a microscope stage and the emission intensity of both B-SWCNTs and P-SWCNTs recorded at two specific x-y spatial positions. Approximately 0.4 mM of picric acid was then placed into the beaker in which the plant roots were submerged and left for an hour. In FIG. 6B, the intensity of B-SWCNT was observed to quench significantly in response to picric acid at the end of an hour. SWCNT chiralities which are fluorescent at higher wavelengths of >1100 nm, namely the (10,2), (9,4), (7,6), (12,1) and (11,3) chiralities appear to quench more in response to the uptake of picric acid, each reducing by approximately 20% in emission on average. P-SWCNT intensity largely stayed constant for all chiralities used in the experiment allowing it to serve as a reference (inactive) sensor. Importantly, the results demonstrate the ability of the plant to uptake picric acid via the root structure and transport it up the stem and leaves, where it reacts with embedded SWCNT sensors and transmit the detection status via intensity attenuation of SWCNT fluorescence.

The standoff detection and identification of chemical analytes and threats are commonly considered to be the 'holy grail' of detection instruments as they enable detection of chemical threats without contact, avoiding the possibility of any contamination. See, Kotidis, P., Deutsch, E. & Goyal, A. in *Micro-and Nanotechnology Sensors, Systems, and Applications VII* Vol. 9467 (eds T. George, A. Dutta, & M. Islam) (Society of Photo-Optical Instrumentation Engineers (SPIE), 2015), which is incorporated by reference in its entirety. For the development of a standoff system (FIG. 2A), a 900 nm long-pass filter was placed at a short distance in front of the camera lens, allowing only NIR wavelengths from fluorescent SWCNTs to be detected and deflecting reflected 785 nm excitation as well as plant fluorescence (650-800 nm) wavelengths. The plant can be modelled as a sequence of reactors in series. Two different camera set-ups were used for this study—a 2D array InGaAs detector (Princeton Instruments OMA V), as well as a Raspberry Pi® (IR filters removed) CCD detector which was used in the development of a miniaturized standoff detection set up (as will be described later).

The emission intensity of the plant under laser excitation was monitored throughout the experiment at a distance of 0.85 m. Picric acid (400 μM) was introduced via a pipette, and the NIR emission intensity of both B-SWCNTs and P-SWCNTS (bright field images in FIG. 2B were monitored at 1-minute intervals for >80 mins. Changes in SWCNT emission intensities can be observed in FIG. 2B (false colored for clarity). P-SWCNT and B-SWCNT indicated by black and red arrows respectively. Temporal changes in nIR fluorescence of a plant infiltrated with B-SWCNT and P-SWCNT is monitored as picric acid is transported from the roots to the leaves via the plant vascular system. While P-SWCNT nIR fluorescence remains stable, the B-SWCNT intensity drops as leaves transpire a solution of picric acid (400 μM) in 10 mM KCl. nIR images were taken with a 900 long pass filter. SWCNT inside leaves were excited with 785 nm laser at 15 mW. P-SWCNT nIR fluorescence remains stable throughout the duration of the experiment. B-SWCNT intensity was observed to drop as picric acid is transported from the roots to the leaves via the plant vascular system. This occurs approximately 5-15 mins after picric acid was first introduced on the roots. Interestingly, the quenching of B-SWCNT fluorescence appears to occur directionally across the leaf surface, away from the mid-rib of the leaf and across the leaf lamina at a rate of approximately 0.2-0.5 mm/min. This can be attributed to the plant transporting picric acid up the vascular system from the roots and stem into the leaf petiole and the midrib, before diffusing across the leaf lamina via minor veins and parenchyma tissues. Picric acid appears to diffuse across the leaf lamina at a rate of 0.32 mm/min which is consistent with bulk flow in the mesophyll cells. It is also observed that at t=36 min, the nIR emission from B-SWCNT appears to split into two individual spots (FIG. 2B, 36 min), which could be attributed to minor veins or stomatal aperture heterogeneity that leads to differential transport rates across the leaf lamina. The monitoring of nIR emission intensity attenuation from embedded sensors provides for the first time, an easy visual mechanism for the monitoring of analyte (nitroaromatic) transport in the whole leaf structure.

Figure 3B:
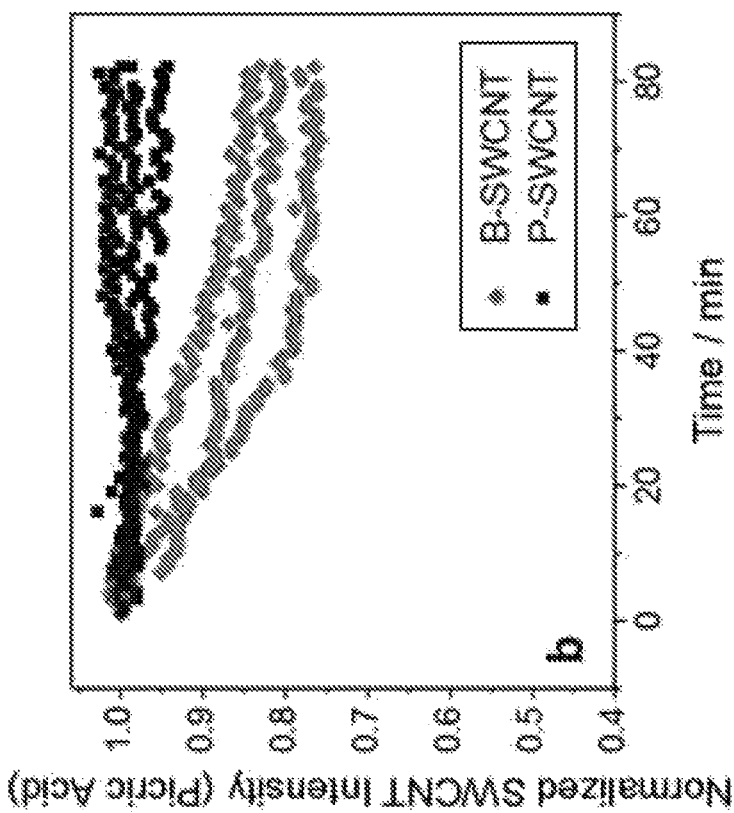
FIGS. 3A-3H show monitoring of B-SWCNT/P-SWCNT nIR intensity ratio (B-SWCNT/P-SWCNT) enables detection of picric acid by nanobionic plants.
Figure 3A:
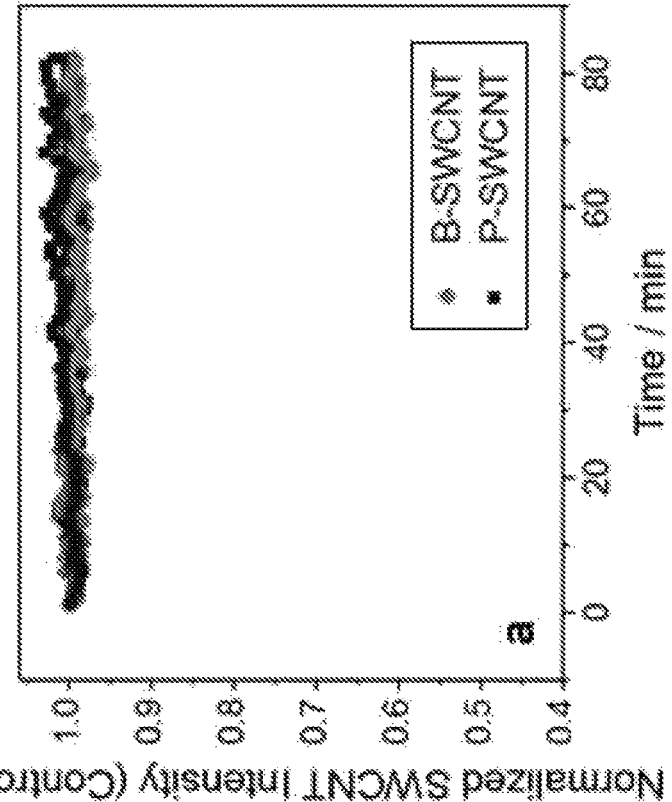
Figure 3D:
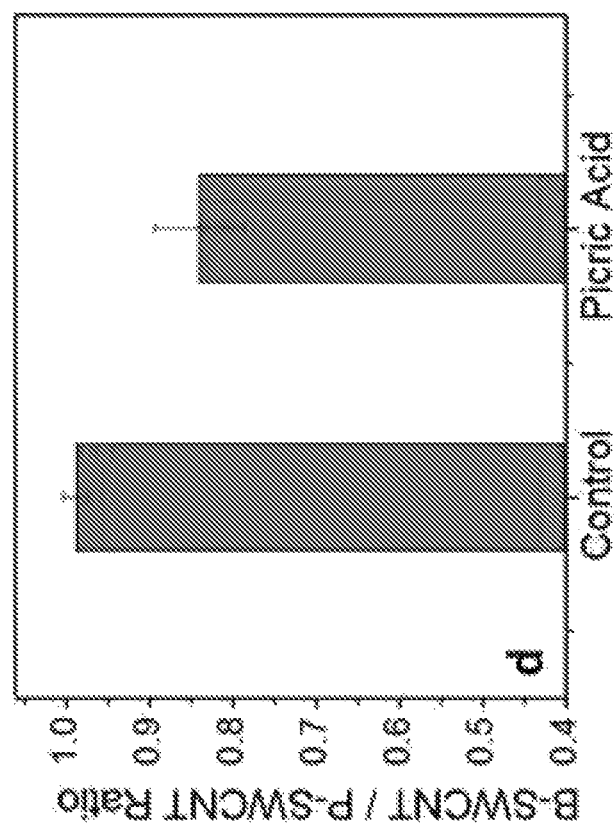
Figure 3C:
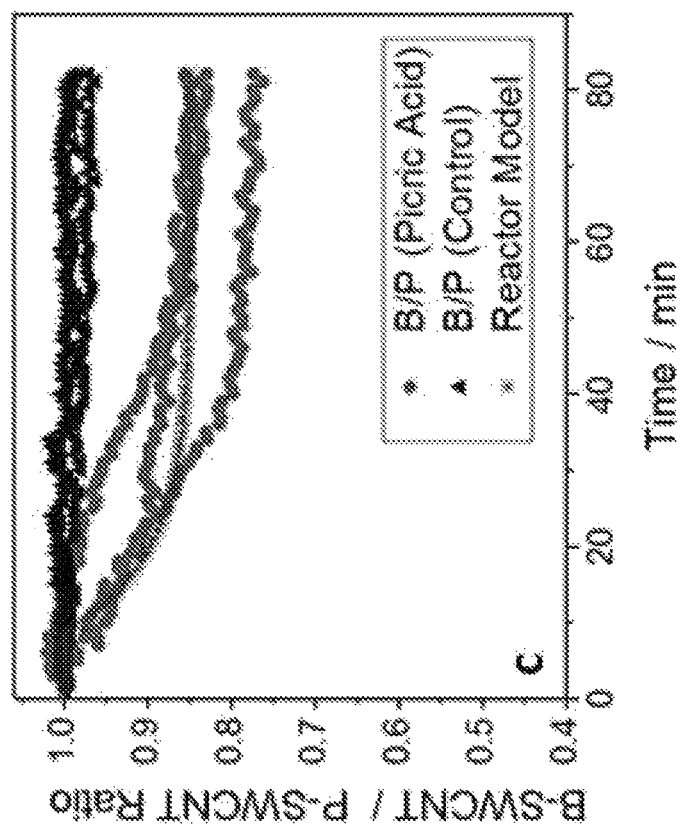

The nIR fluorescence intensity of embedded P-SWCNT and B-SWCNT in response to uptake of picric acid and water (control) was studied in several individuals of spinach plants. In FIGS. 3A-3F, leaves with SWCNTs infiltrated were excited with 785 nm laser at 15 mW. Then nIR fluorescence of leaves infiltrated with B-SWCNT and P-SWCNT is monitored in real time as plants transpire a solution of 0.4 mM of picric acid or 10 mM KCl (control). Both P-SWCNT and B-SWCNTs were relatively invariant with the uptake of water (FIG. 3A), while only B-SWCNT showed intensity attenuation in response to picric acid (FIG. 3B) as previously observed. The ratio of B-SWCNT to P-SWCNT (B/P ratio) was used to determine detection of picric acid by the plant. A ratiometric approach has unique advantages compared to the single intensity approach, which includes reducing the effects of mild dilution (leakage) caused by water transport through the leaf, minor orientation changes of the leaf and instrument fluctuation. See, Feng, Y., Cheng, J., Zhou, X. & Xiang, H. Ratiometric optical oxygen sensing: a review in respect of material design. *Analyst* 137, 4885-4901 (2012), Gryczynski, Z., Gryczynski, I. & Lakowicz, J. Fluorescence sensing methods. *Methods Enzymol.* 360, 44-75 (2002), and Badugu, R., Lakowicz, J. & Geddes, C. Excitation and emission wavelength ratiometric cyanide-sensitive probes for physiological sensing. *Analytical Biochemistry* 327, 82-90 (2004), each of which is incorporated by reference in its entirety. The B/P ratio started decaying 5-15 min after picric acid was first introduced to the solution in which the roots of the plant were submerged, then reaching a plateau at about 40-50 min (FIG. 3C). The residence time function of picric acid as it travels up the plant is calculated using the reactor model (Eq. (3)) and plotted in FIG. 3C. On average, the B/P ratio dropped to 85% of the initial value 50 min after picric acid was first introduced (FIG. 3D). Two-tailed P value of 0.0061 indicates a statistically significant difference between the control samples and the samples that were exposed to picric acid (n=4 (picric acid); n=3 (control)). The variability between each experimental run can be attributed to individual differences in root permeability to picric acid, varying leaf transpiration rates, and also whole plant conductance rates. Together, these variations can lead to different residence times in each part of the plant, which affect the overall response rate of the nanobionic plant sensor.

Figures 3E, 3F:
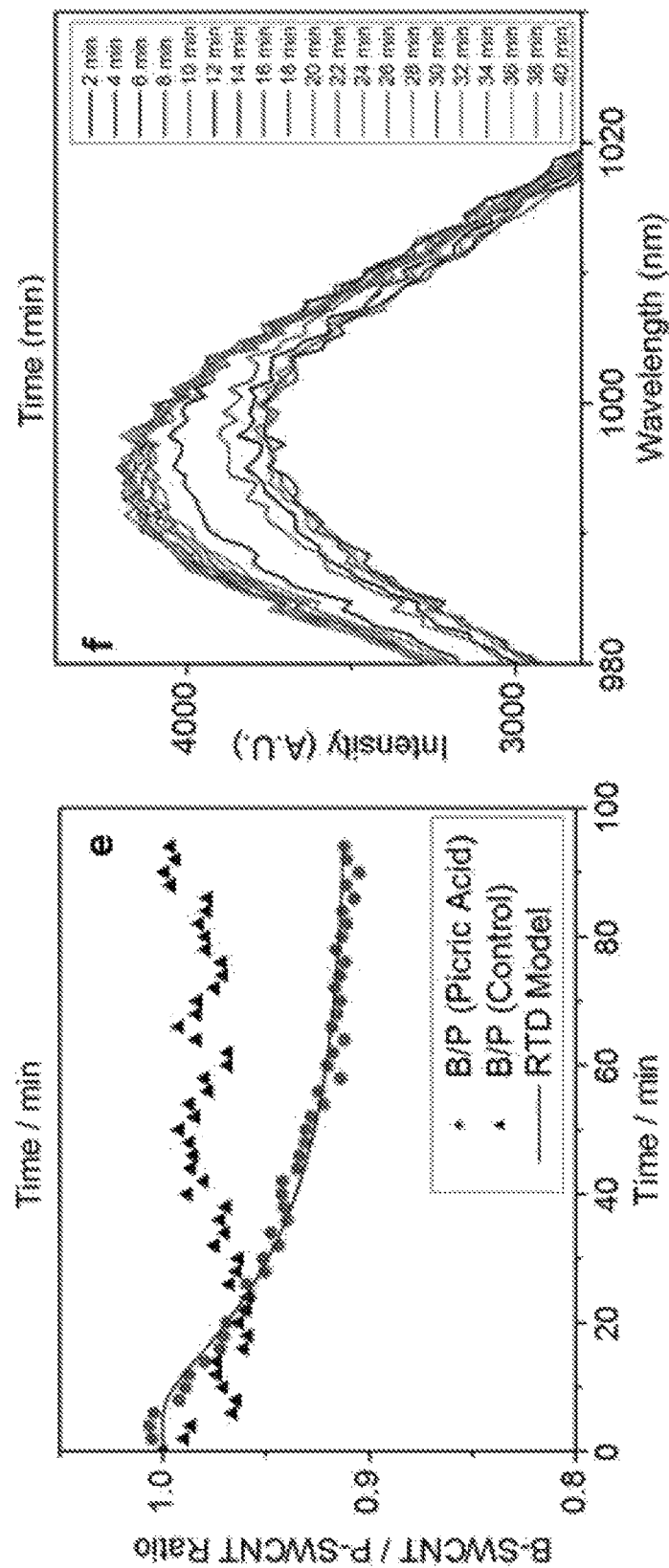
Figure 3G:
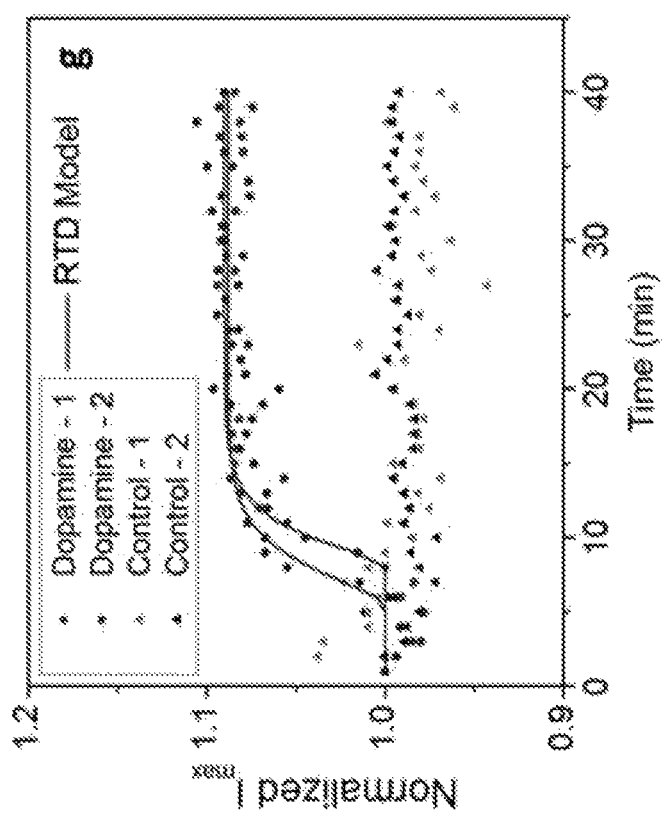
Figure 3H:
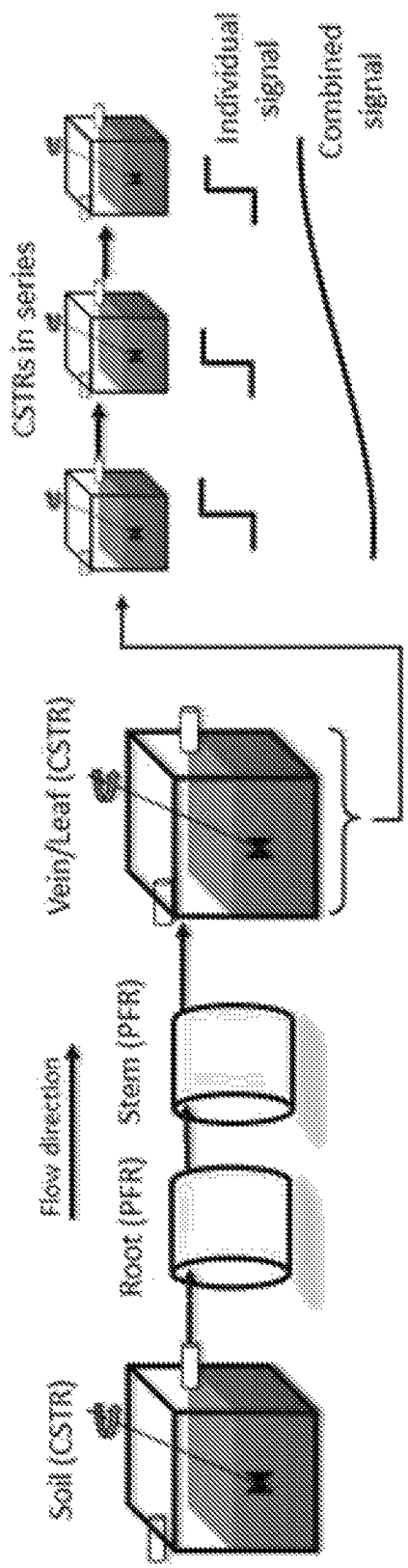

To demonstrate the generalizability of the platform, a nanobionic dopamine detecting plant was developed utilizing $(GT)_{15}$-SWCNT infiltrated into plants as a turn-on fluorescent sensor for dopamine in the groundwater. $(GT)_{15}$-SWCNT have been previously shown to be sensitive to changes in dopamine concentration, with a turn-on response due to an increase in the fluorescence quantum yield. See, Kruss, S. et al. Neurotransmitter Detection Using Corona Phase Molecular Recognition on Fluorescent Single-Walled Carbon Nanotube Sensors. *J. Am. Chem. Soc.* 136, 713-724 (2014), which is incorporated by reference nin its entirety. Dopamine exerts significant physiological influence on plant growth and has been shown to affect root growth and enzyme activity in (soybean) seedlings, See, Guidotti, B., Gomes, B., Siqueira-Soares, R. C., Soares, A. C. & Ferrarese-Filho, O. The effects of dopamine on root growth and enzyme activity in soybean seedlings. *Plant Signal Behav.* 8, e25477 (2013), which is incorporated by reference in its entirety. A 10% response was observed (FIGS. 3F and 3G) in the spectral intensity as measured with a InGaAs detector coupled with a spectrograph when the plant transpires a solution of dopamine (100 μM), which is lower than the range of concentrations used by Guidotti et al. in their study. The gradient of the response is significantly steeper than that of picric acid, which is due to the narrower field of view (from using a 20× objective on a microscope stage) in the dopamine experiment as explained by the residence time distribution model (FIG. 3H).

Figure 2A:
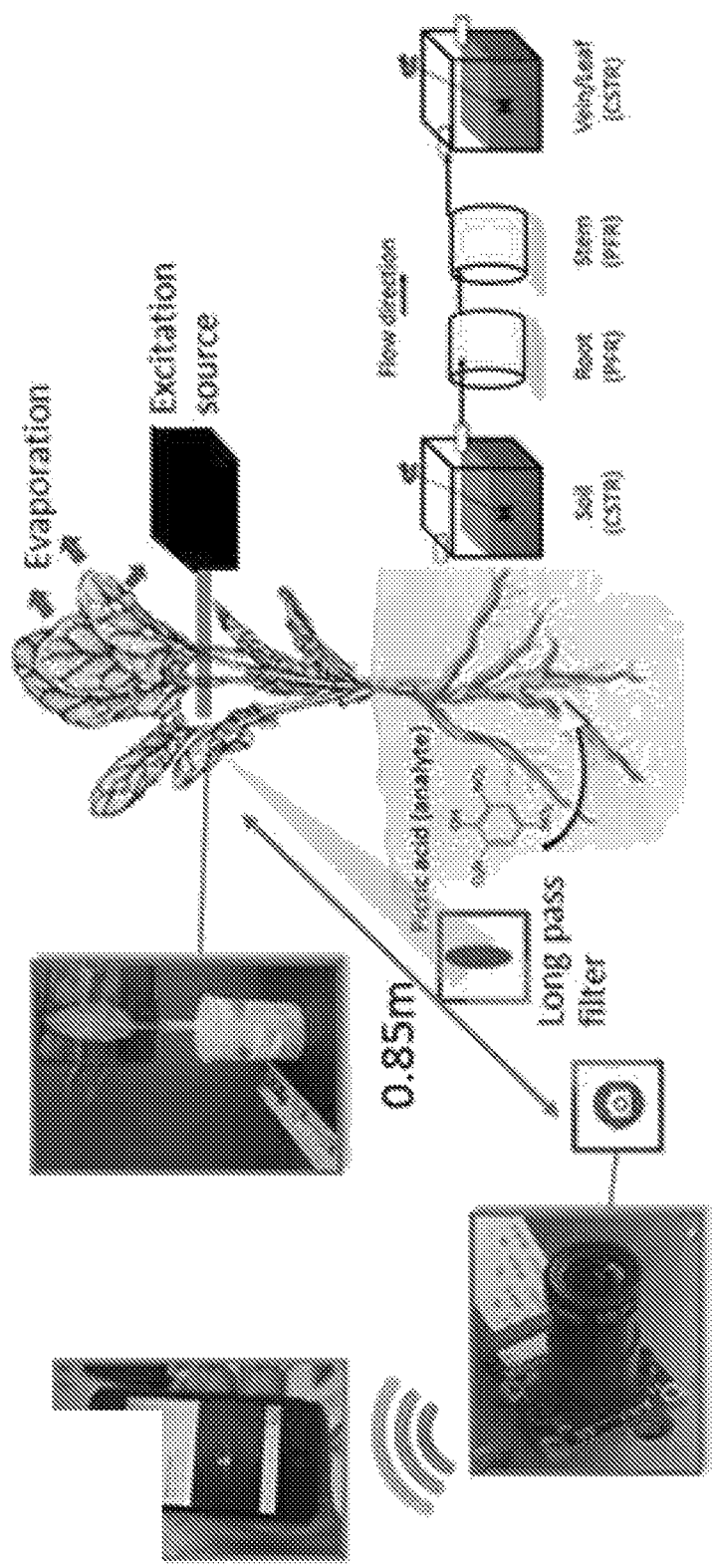
FIGS. 2A-2C show standoff detection of picric acid using nanobionic spinach plant.
Figure 2B:
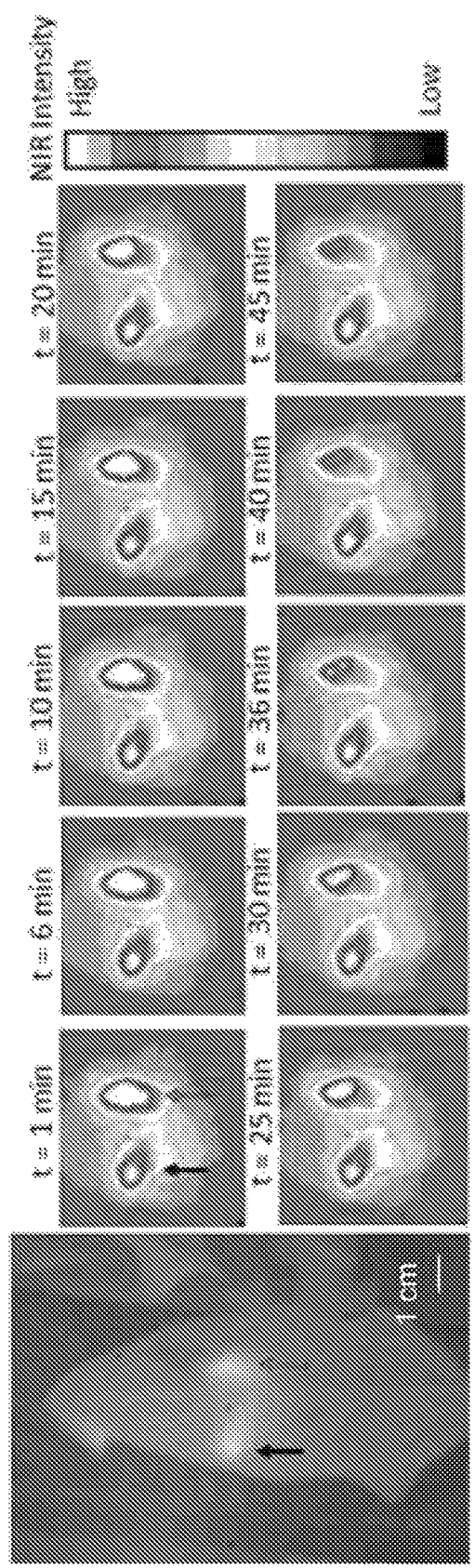

The observed results can be explained using a reactor model (FIG. 2A (right)) which considers the plant as being a sequence of continuous stirred tank reactor (CSTR) or plug flow reactor (PFR). A CSTR is an idealized perfectly mixed reactor where the output composition is identical to the composition of the material inside the reactor. See, Fogler, S. *Elements of chemical reaction engineering.* 4 edn, (Person Education, 2006), which is incorporated by reference in its entirety. A PFR assumes that the fluid within the reactor is perfectly mixed in the radial direction but not in the axial direction, and the fluid can be seen as being a series of infinitely thin coherent "plugs". The beaker containing picric acid is modeled here as a continuous stirred tank reactor with slow mixing (Eq. (1)). The roots and stem are modeled as individual plug flow reactors (Eq. (2)), where the analyte is transported through the plant via the vasculature system. The leaves of the plant are modeled as CSTRs, where the analyte exits the leaf veins and diffuses into surrounding mesophyll cells in the leaf lamina. Eq. (1)-(2) are described as follows:

$$f_{CSTR}(t) = \frac{1}{\tau} e^{t/\tau} \quad (1)$$

where $f_{CSTR}$ is the residence time distribution function (CSTR) and $\tau$ is the reactor residence time and $$f_{PFR}(t) = \delta(t-\tau) \quad (2)$$

where $f_{PFR}$ is the residence time distribution function of a PFR

An overall cumulative distribution function for the sequence of reactors (Eq. (3)) can be obtained by taking the Laplace transform of the residence time distribution functions as shown in Table 1 and applying the convolution theorem:

$$F(t) = H(\tau_R)H(\tau_S)H(-\tau_R - \tau_S + t)\left(\frac{e^{\frac{-\tau_R-\tau_S+t}{\tau_{soil}}}}{\tau_{soil} - \tau_L} - \frac{e^{\frac{-\tau_R-\tau_S+t}{\tau_L}}}{\tau_{soil} - \tau_L}\right) \quad (3)$$

where $\tau_{soil}$, $\tau_R$, $\tau_S$ and $\tau_L$ are the residence times for the soil, root, stem and leaf respectively and H represents the Heaviside function. The residence times are a function of the hydraulic conductances of the plant, which is typically within an order of magnitude in the same species, particularly in leaves. There exist very few studies on plant hydraulics for *Spinacia olecerea*, and here the calculations are based on work done by Swaef and coworkers on Tomato plants. See, de Swaef, T., Verbist, K., Cornelis, W. & Steppe, K. Tomato sap flow, stem and fruit growth in relation to water availability in rockwool growing medium. *Plant Soil* 350, 237-252 (2012), which is incorporated by reference in its entirety. In tomatoes, water flow was found to be at a maximum of 100 g/hr (1.6 ml/min). Taking the geometry of the spinach stems to be a cylinder (5 cm long by 0.5 cm wide), the residence time in the stem ($\tau_S$) can be calculated to be approximately 3-6 min. Accordingly, $\tau_L$ can be typically estimated to be about ≥30% of the resistance of the whole plant (see, Sack, L. & Holbrook, N. M. Leaf hydraulics. *Annu. Rev. Plant Biol.* 57, 361-381 (2006), which is incorporated by reference in its entirety), giving a residence time of 5-10 mins. The leaf hydraulic conductance for tomatoes and other crop herbaceous plants (used as a proxy for spinach) have been measured to be approximately 2.0 mmol m$^{-2}$ s$^{-1}$ MPa$^{-1}$. See, Giraldo, J. P., Wheeler, J. K., Huggett, B. A. & Holbrook, N. M. The role of leaf hydraulic conductance dynamics on the timing of leaf senescence. *Functional Plant Biol* 41, 37-47 (2014), and Sack, L. & Holbrook, N. M. Leaf hydraulics. *Annu. Rev. Plant Biol.* 57, 361-381 (2006), each of which is incorporated by reference in its entirety. Using a typical leaf water potential of 0.1-1 MPa and a leaf area of approximately 1.5×10$^{-3}$ m$^2$, the flow rate through a leaf can be estimated to be between 0.003-0.03 mmol s$^{-1}$. Assuming a leaf cross sectional area to be approximately 2.2×10$^{-5}$ m$^{-2}$, the flow rate across a leaf sectional area is 0.15-1.5 mm/min, with the exact value dependent on species, hydration, temperature, and irradiance. See, Sack, L. & Holbrook, N. M. Leaf hydraulics. *Annu. Rev. Plant Biol.* 57, 361-381 (2006), which is incorporated by reference in its entirety. Finally, the roots of a plant typically possesses lower hydraulic resistance than stems, and the residence time is assumed to be approximately 2-5 mins, or approximately 15-20% of the hydraulic resistance of the whole plant.

The use of the normalized residence time (mm/mm) allows one to account for the effect of different field of views. A larger field of view would be modelled as a CSTR with correspondingly longer residence time and vice versa. For instance, a field of view of 8-10 mm (length) of functionalized leaf is modelled as a CSTR with a residence time of approximately 6-66 min while a 0.4 mm field of view is modelled as a CSTR with a residence time of approximately 0.3-8 min.

Figure 7:
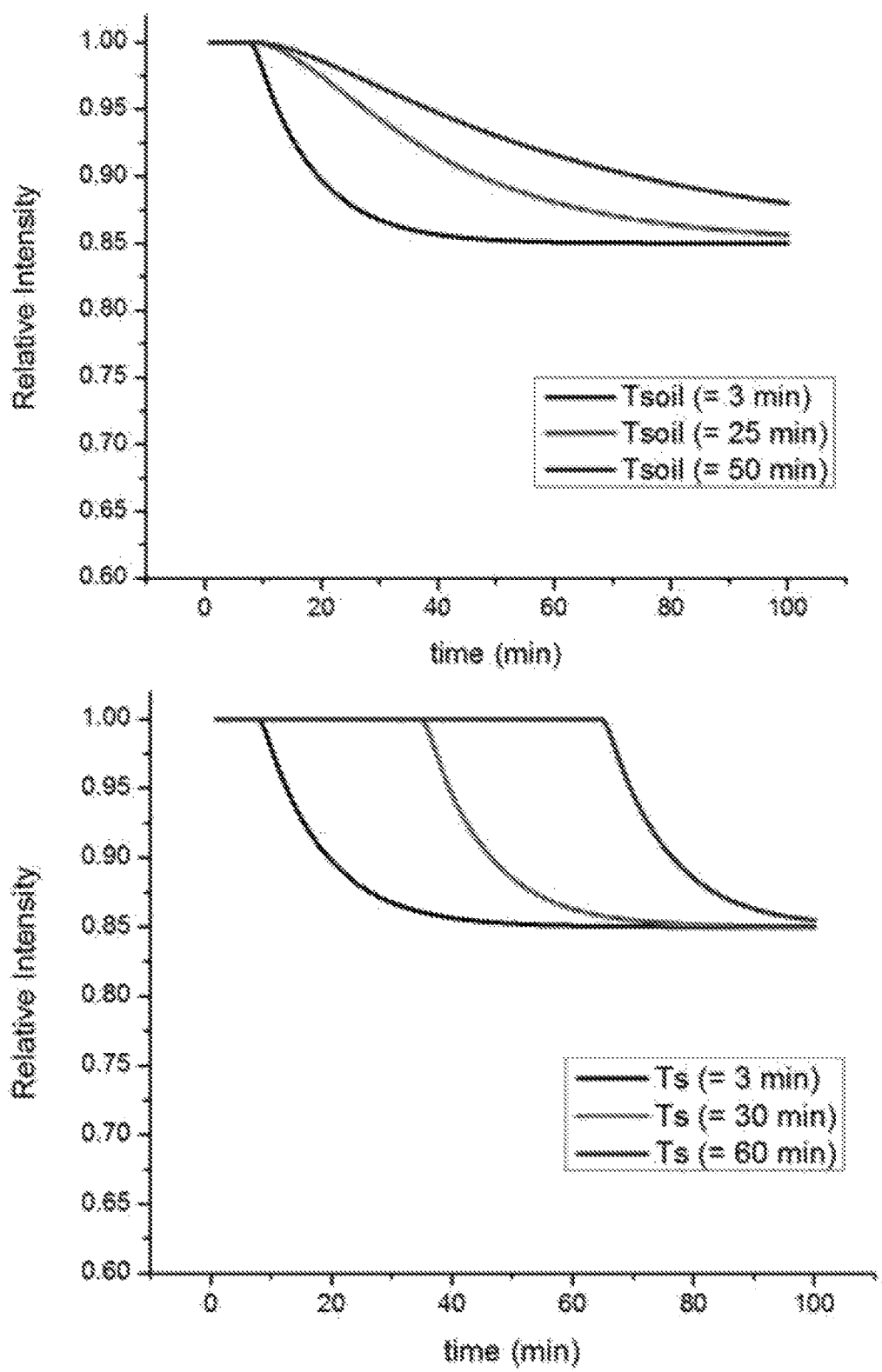
FIG. 7 shows a plant reactor model.

Using the above parameters for the flow rate of fluid through the plant (Table 2), and scaling to account for the average amount of fluorescence quenching observed, a plant reactor model can be mathematically described, and which shows a good fit with experimental observations (FIG. 3D). The model described in Eq. (3) was used to fit the experimental data (FIGS. 3C, 3E and 3G). For the estimation of $\tau_L$, the residence time of leaf was scaled with the field of view of individual quenching experiment, while $\tau_R$ and $\tau_S$ were calculated as one singular parameter contributing to the time delay of sensor response. The variation in the reactor model output in response to varying $\tau_{soil}$ and $\tau_S$ is shown in FIG. 7 and can provide a mathematical understanding of the variation in intensity quenching (FIG. 3C). FIG. 7 shows the effect of varying soil and stem residence times. Long residence times in the soil (slower uptake into the plant) leads to a gentler gradient in the intensity response, where a longer time is needed before the sensor becomes saturated. An increase in the residence time in the stem, $\tau_S$ (time for analyte transport up the plant into the leaves) leads to a delay before the first quenching response of the embedded sensors is observed. Given the heterogeneity in root permeability, as well as differences in total stem and vein conductances, the residence times in the soil and in the stem/leaf is likely to vary from plant to plant, which would lead to varying response rates as seen in experimental observations (FIG. 3)), as well as the significant standard deviations in the residence times observed. The calculated (fitted) residence times in the leaf is consistent with the experimentally observed residence time of 0.2-0.5 mm/min on average, suggesting that the aforementioned assumptions are justified.

TABLE 1

Plant module and reactor residence time distribution function

| Plant Module | Residence time distribution function, f(t) | Residence time-Laplace transformed (s) |
|---|---|---|
| Soil (CSTR) | $\frac{1}{\tau_{soil}} e^{t/\tau_{soil}}$ | $\frac{1}{S\tau_{soil}+1}$ |
| Root (PFR) | $\delta(t - \tau_R)$ | $H(\tau_R)e^{-s\tau_R}$ |
| Stem (PFR) | $\delta(t - \tau_S)$ | $H(\tau_S)e^{-s\tau_S}$ |
| Vein/Leaf (CSTR) | $\frac{1}{\tau_L} e^{t/\tau_L}$ | $\frac{1}{S\tau_L+1}$ |

TABLE 2

Estimated physical parameters for plant reactor model*

| Physical Parameters | Approximate value/min | Remarks |
|---|---|---|
| $\tau_{soil}$ | 0.5-2 | $\tau_{soil} = \frac{V_{soil}\phi_{soil}}{F}$ |
| $\tau_R$ | 2-5 | $\tau_R = \frac{nA_{root}L_{root}}{F}$ |
| $\tau_S$ | 3-6 | $\tau_s = \frac{nA_{stem}L_{stem}}{F}$ |
| $\tau_L$ | 5-10 | $\tau_L = \frac{V_{meosphyll}\phi_{leaf}}{F_{leaf}}$ |

*See, Sack, L. & Holbrook, N.M. Leaf hydraulics. *Annu. Rev. Plant Biol.* 57, 361-381 (2006), and de Swaef, T., Verbist, K., Cornelis, W. & Steppe, K. Tomato sap flow, stem, and fruit growth in relation to water availability in rockwool growing medium. *Plant Soil* 350, 237-252 (2012), each of which is incorporated by reference in its entirety.

Miniaturized and Portable Detection System

Figure 2C:
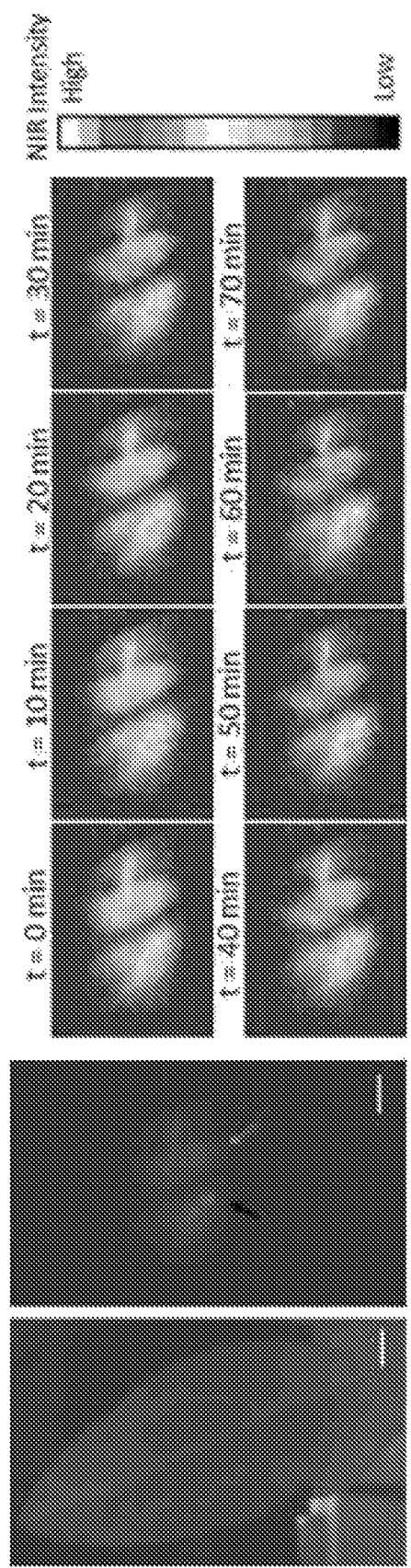

A practical prototype for the monitoring of the explosive sensing plant was developed through the use of a Raspberry Pi® coupled with a CCD detector module (IR filters removed) in place of the Princeton Instruments OMA V detector. The camera module provides a 5-megapixel native resolution with a sensor-capable of 2592×1944 pixel static images (similar to most cameras found in smartphones). The silicon detector is typically sensitive up to the near infrared (~1100 nm; see Held, G. *Introduction to light emitting diode technology and applications.* 116 (CRC Press, 2008), which is incorporated by reference in its entirety). An exposure time of 6 s at ISO 800 was used to capture a time lapse video of the sensor plant at two minute intervals. This RaspberryPi® stand-off detection set up is able to monitor the SWCNT near-infrared fluorescence (both P-SWCNT and B-SWCNT as shown in FIG. 2C (brightfield)) that were infiltrated into the leaves of Spinach plants (FIG. 2C, brightfield), confirming its suitability as a practical standoff detector. In FIG. 2C, nIR emission from embedded P-SWCNTs (black arrow) and B-SWCNTs (red arrow) is visualized with 785 nm laser excitation (15 mW) (center) (Scale bar: 1 cm). FIG. 2C, right, shows false colored time lapse pictures similarly show temporal changes in nIR fluorescence of a plant infiltrated with B-SWCNT and P-SWCNT as picric acid is transported from the roots to the leaves via the plant vascular system.

Figure 5:
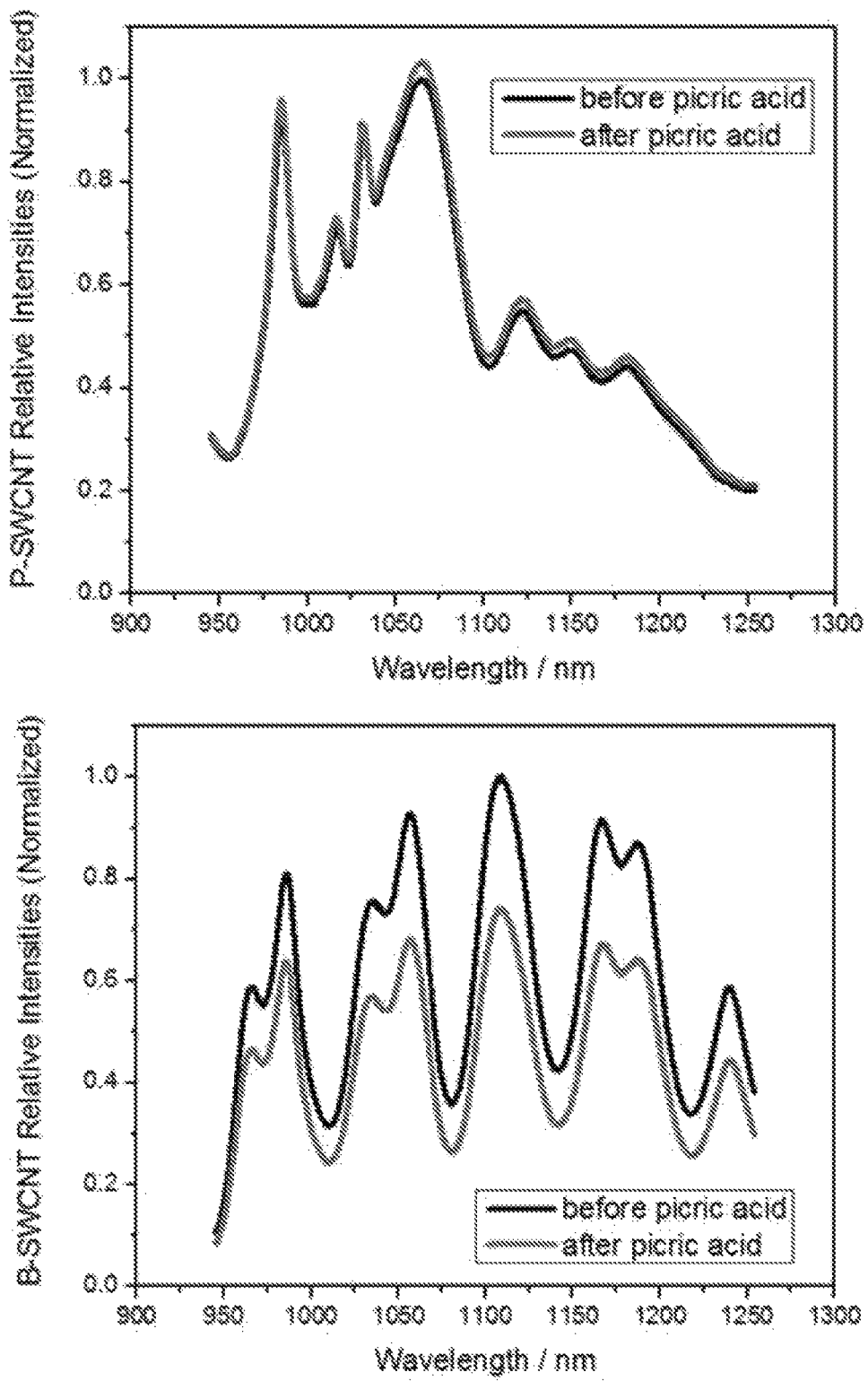
FIG. 5 shows NIR fluorescence spectra of PVA-SWCNT and Bombolitin-SWCNT in response to picric acid in vitro.

This miniaturized detection system was then applied for the detection of nitroaromatics via root uptake (FIG. 2C (false colored images) and FIG. 3E). The B/P ratio was observed to decay in response to picric acid (1.2 mM) after approximately 8 mins, and plateaus at about 90% of the original value. The lower degree of quenching of the B/P intensity can be attributed to the fact that the RaspberryPi CCD detector is less sensitive at higher wavelengths above 1100 nm, unlike the InGaAs detector which is sensitive up to 1600. This result in a more muted response as B-SWCNT chiralities which fluoresce at higher wavelengths are more sensitive to the presence of picric acid (FIGS. 5 and 6A-6B). This system will be especially useful for functionalized SWCNT chiralities that emit at wavelengths below 1100 nm, where the silicon CCD detector is most sensitive. Besides portability, low cost and energy requirements, the RaspberryPi® monitoring system also enables easy connectivity via the Internet. The system is programmed to send periodic near-infrared fluorescence images via email to the end user, enabling long-distance monitoring of nitroaromatics from any location. This system can be easily extended to include different sensors embedded in plants, potentially enabling the surreptitious and self-powered real time monitoring of the environment via nIR hand-held devices.

Several attempts have been made to make synthetic materials capable of replicating transpiration in plants so as to enable new approaches to extract water from subsaturated soils, or to enable processes which require large pressure differences to be performed passively. See, Wheeler, T. D. & Stroock, A. D. The transpiration of water at engative pressures in a synthetic tree. *Nature* 455, 208-212 (2008), which is incorporated by reference in its entirety. However, a key challenge is in maintaining a continuous water column in a negative pressure environment. At large tensions (on the order of several MPa) in the plant, the water column can be easily broken by air seeding. Furthermore, the heterogeneity and fragility of synthetic materials utilized such as nanoporous ceramics limits their practical use. See, Guan, Y. & Fredlund, D. G. Use of the tensile strength of water for the direct measurement of high soil suction. *Can. Geotech J.* 34, 604-614 (1997), which is incorporated by reference in its entirety. Plants however, have a hydraulic architecture with a redundant network of vessels to protect them from catastrophic failure. They can also refill the vessels by generating root pressure. The nanobionic plant hybrid sensor exploits the natural advantages of the plant. The energy expanded for the equivalent in pulling up the dissolved analyte from the ground (with mass flow rate taken to be approximately $1.5 \times 10^{-6}$ kg/s) is estimated to be 1.03 µW for a spinach plant that is approximately 7-10 cm tall. This energy is supplied by natural transpiration, and not a user-supplied power source.

Figures 4A, 4B:
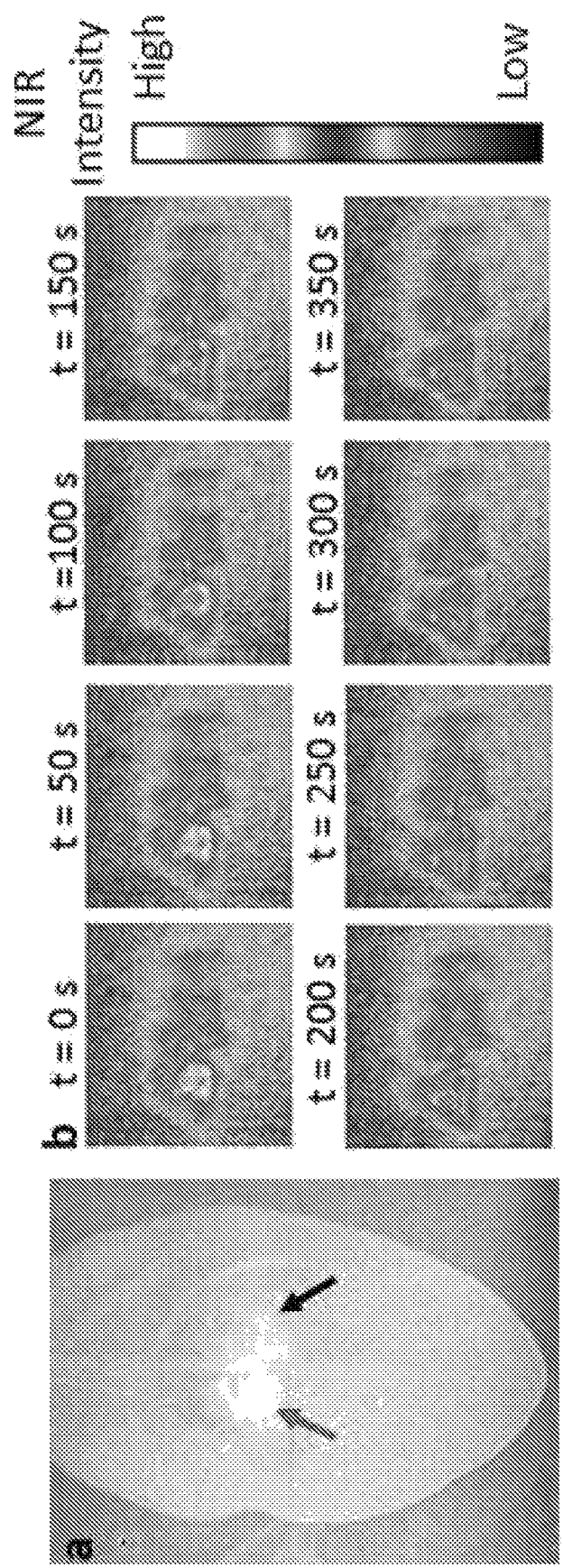
FIGS. 4A-4E show nIR response of B-SWCNT and P-SWCNT to picric acid sprayed on the lamina of a spinach leaf.
Figure 4D:
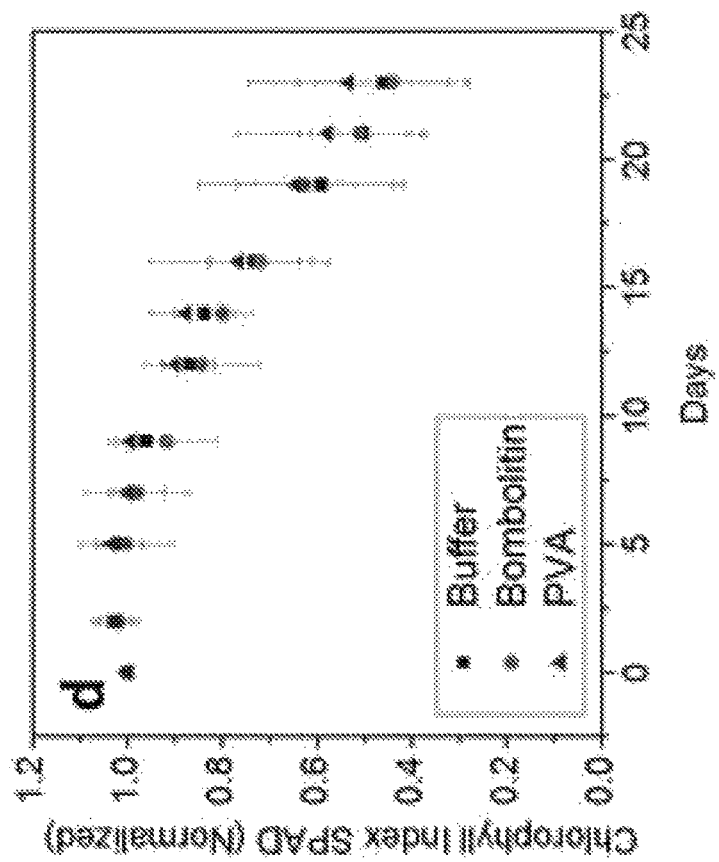
Figure 4C:
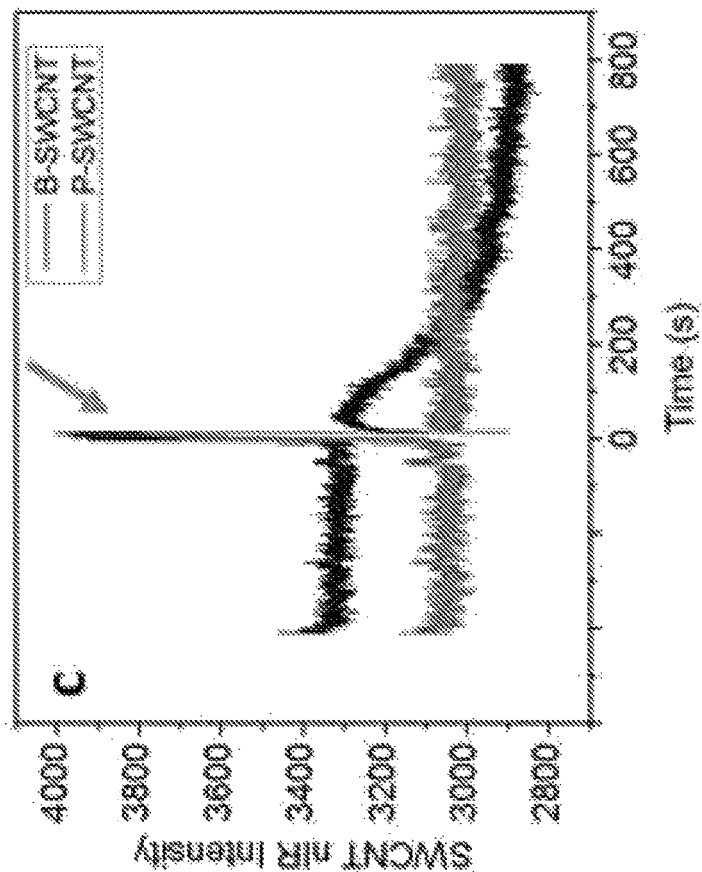
Figure 4E:
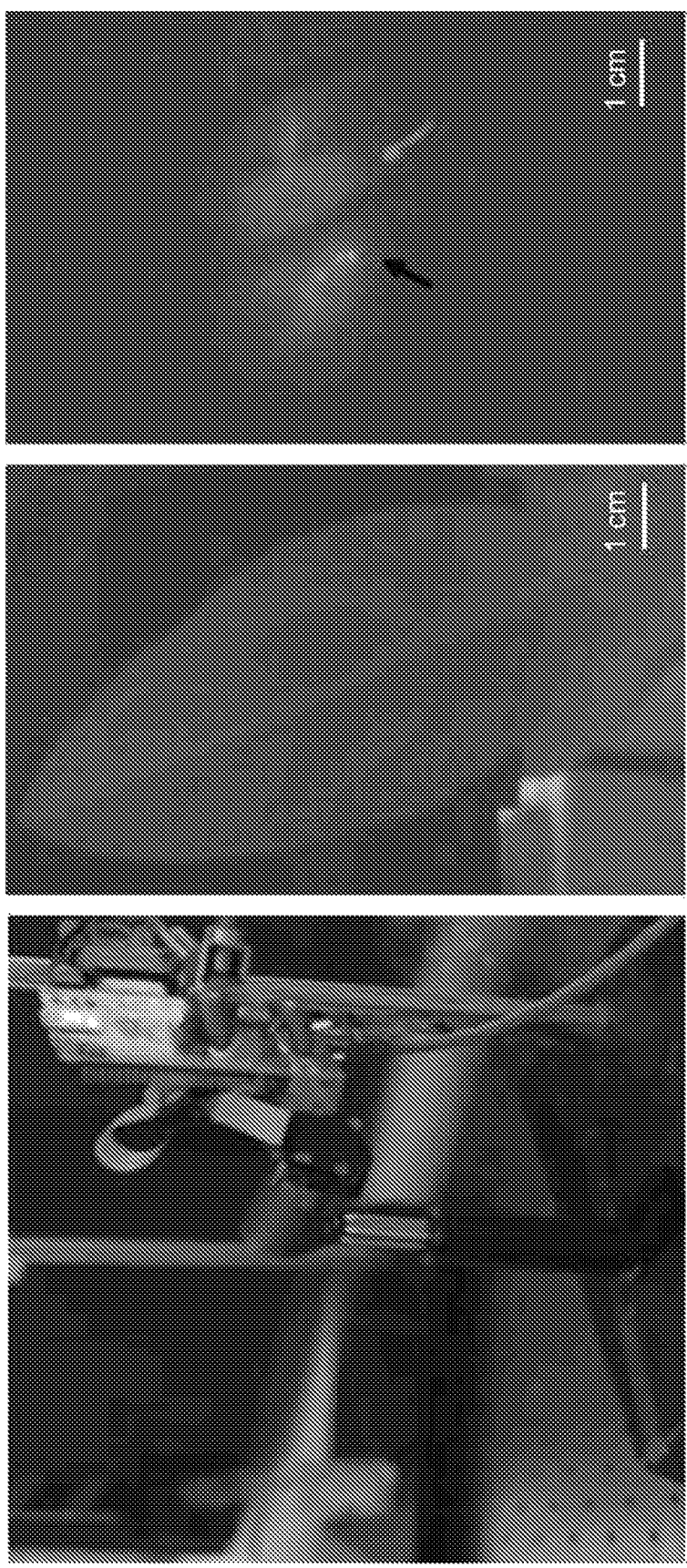

FIG. 4E shows the use of the nanobionic plant as an autosampler of groundwater and how it is coupled to a practical standoff detection set up built upon the RaspberryPi SWCNT nIR emission can be detected by a RaspeberryPi® CCD detector (IR filters removed) and transmitted wirelessly and in real time via email interface to a smartphone (left). Bright field image of spinach plant infiltrated with SWCNT sensors (center). nIR emission from embedded P-SWCNTs (black arrow) and B-SWCNTs (red arrow) is visualized with 785 nm laser excitation (15 mW) (right). This system can be easily extended to include different sensors embedded in plants, potentially enabling the surreptitious and self-powered real time monitoring of the environment via nIR hand-held devices.

Figure 11:
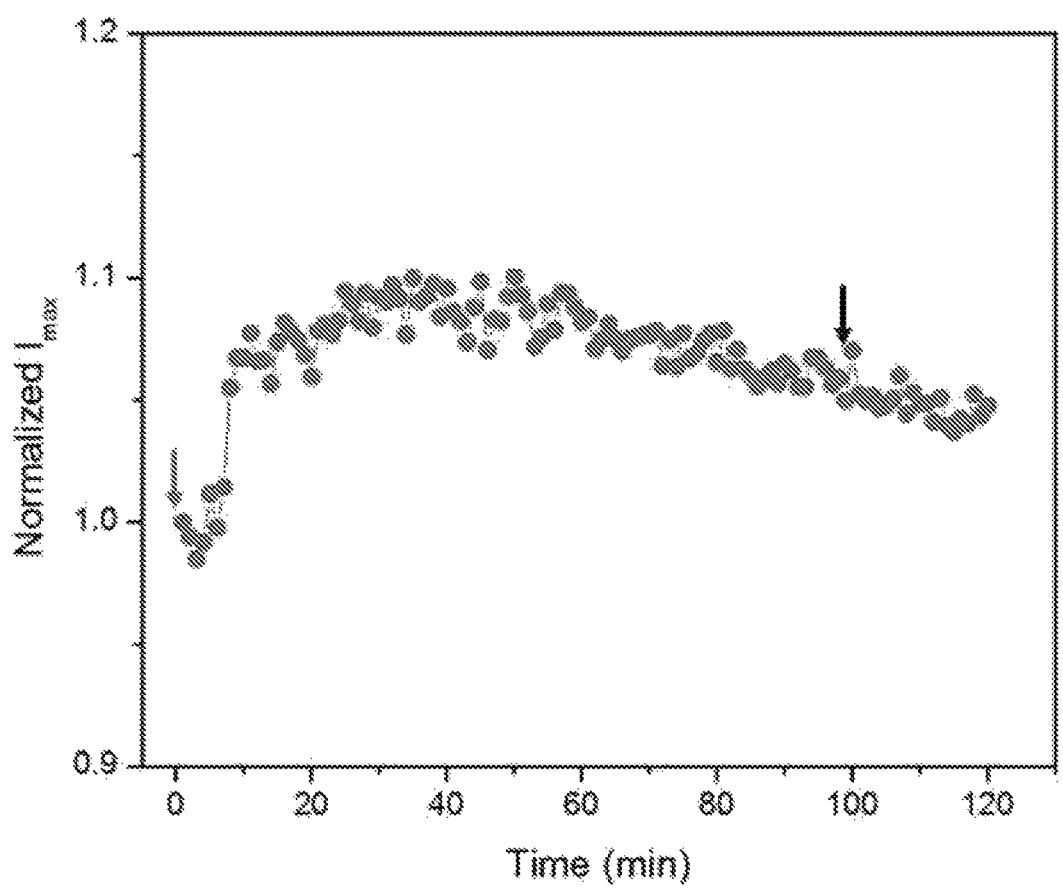
FIG. 11 shows $(GT)_{15}$-SWCNT emission spectra tracked with time as plants transpire a solution of dopamine.

The approximate water flow rate and accumulation ratio reported by Swaef and Schneider respectively (see de Swaef, T., Verbist, K., Cornelis, W. & Steppe, K. Tomato sap flow, stem and fruit growth in relation to water availability in rockwool growing medium. *Plant Soil* 350, 237-252 (2012), and Schneider, K., Oltmanns, J., Radenberg, T., Schneider, T. & Mundegar, D. Uptake of nitroaromatic compounds in plants. *Environ. Sci. & Pollut. Res.* 3, 135-138 (1996), each of which is incorporated by reference in its entirety) were utilized to estimate the accumulation rate of nitroaromatics in a spinach leaf as approximately 0.7-1.3 nmol/min, dependent upon the concentration of nitroaromatics in the soil. In using the plant as a chemical sensor, the chemical potential of the analytes near the sensor is likely persistent or increasing as analytes are transported from the roots to the aerial tissues and accumulates in the leaves (assuming a much slower rate of analyte breakdown compared to sensor response rate), resulting in the plant sensor saturating and behaving like an irreversible sensor (FIG. 11). FIG. 11 shows $(GT)_{15}$-SWCNT emission spectra is tracked with time as plants transpire a solution of 100 µM of dopamine (left arrow). A turn on response of approximately 10% is observed and the signal gradually diminishes with time. A second addition of 1 mM dopamine (right arrow) does not show response recovery, suggesting sensor saturation. Upon exposure to a stream of any concentration of analyte, irreversible sensors will ultimately respond and eventually saturate (see Chang, Y. L. & Strano, M. S. Understanding the dynamics of a signal transduction for adsorption of gases and vapors on carbon nanotube sensors. *Langmuir: the ACS journal of surfaces and colloids* 21, 5192-5196 (2005), which is incorporated by reference in its entirety), and it is inappropriate to report a detection limit for a sensor of this kind. Furthermore, the observed response time and magnitude of the sensor response is dependent on root permeability to the analyte, analyte stability in the plant, sensor stability, plant transport rates, and sensitivity of the detector.

Standoff Detection of Nitroaromatics Via Leaf Uptake

The ability of standoff nitroaromatic detection via leaf cuticle uptake was also investigated, using excised spinach leaves infiltrated with B-SWCNT and P-SWCNT sensors. The functionalized leaf was gently held by double-sided tape on the adaxial side while the leaf abaxial side was exposed to 785 nm laser excitation, in a similar set up as shown in FIG. 2A. A droplet of picric acid (0.2 mL of 0.4 mM) was deposited on the leaf surface leading to droplet movement downwards by gravitational pull. The nIR fluorescence intensity of the leaf under laser excitation was monitored throughout the experiment with the InGaAs standoff detector, at a distance of 0.85 m. The brightfield image of the infiltrated leaf under 785 nm excitation can be seen in FIG. 4A. Upon addition of picric acid on the leaf surface, sharp peaks in emission were observed due to Rayleigh scattering from the analyte droplets (FIG. 4C). In FIG. 4C, the strong peak at time zero corresponds to the Raleigh scattering caused by droplets of picric acid moving on the surface of the leaf lamina (green arrow). B-SWCNT nIR intensity showed a clear quenching response about 10 s after exposure to picric acid, followed by the fluorescence signal reaching a plateau at 400 s. P-SWCNT emission intensity remained invariant after exposure to picric acid. The quenching dynamics can be similarly observed in the false colored time-lapse images in FIG. 4B. An approximate 12% decrease in B-SWCNT intensity was observed 400 s after exposure to picric acid. The decrease in fluorescence was maintained till the end of the experiment (>1200 s). The sensor system developed can potentially allow for sensor multiplexing. The resolution limit in the x-y axis is theoretically given by the pixel size of the detector, which corresponds to approximately 0.5 mm for a standoff distance of 0.85 m.

The dynamics of signal transduction for the sensor response to leaf uptake of picric acid can be similarly obtained by applying Eq. (3), yielding $S_{max}=0.14$ and $k_{leaf}=0.36$ (mM·min)$^{-1}$, which is considerably greater than $k_{root}$. The smaller rate constant of the root uptake mechanism is likely due to the long distances needed for picric acid to travel from the soil to the leaf as well as dilution as picric acid distributes within the plant, which would lead to a slower response rate of the sensor when used as a groundwater sampler. The sensor system developed can potentially allow for sensor multiplexing. The resolution limit in the x-y axis is theoretically given by the pixel size of the detector, which corresponds to approximately 0.5 mm for a standoff distance of 0.85 m.

Regulation of Analyte Residence Times

Figure 8A:
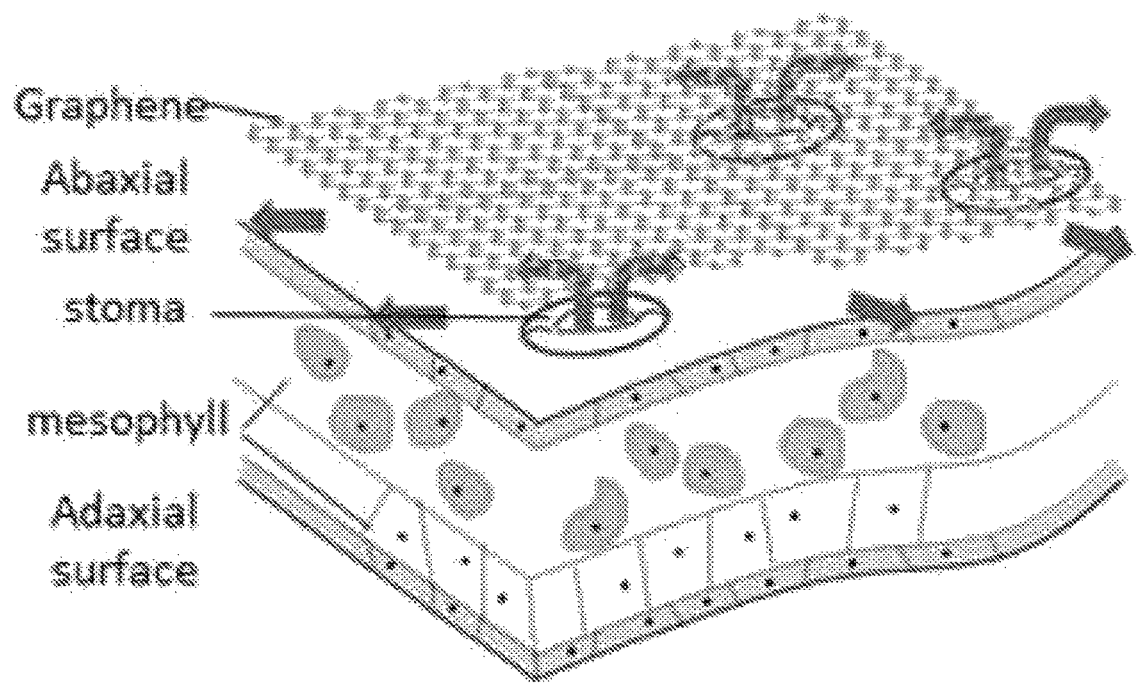
FIGS. 8A-8B show hybrid leafs.
Figure 8B:
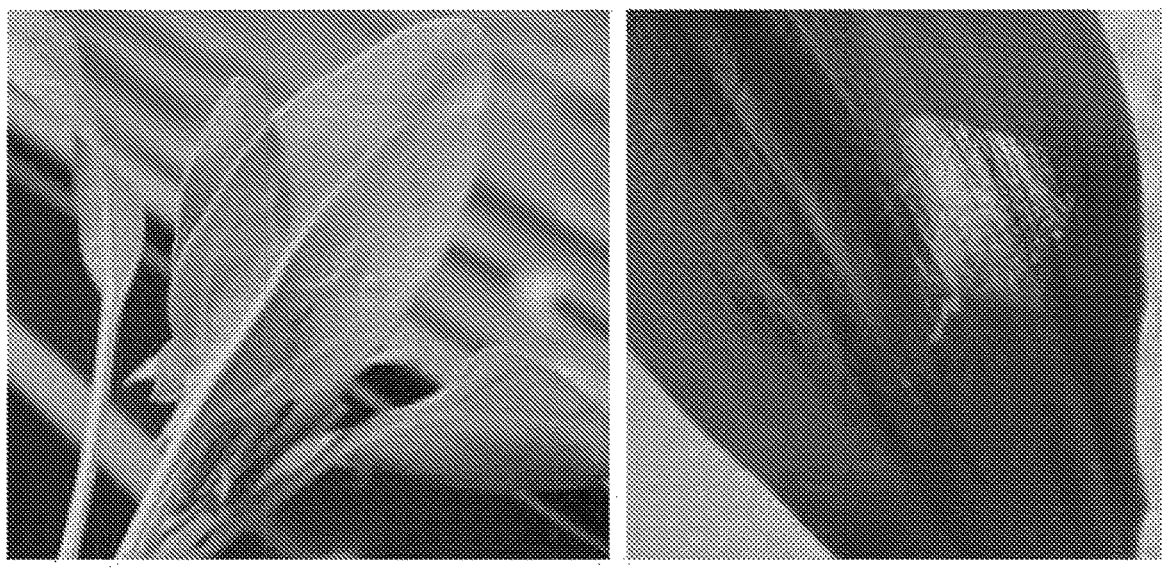
Figure 9A:
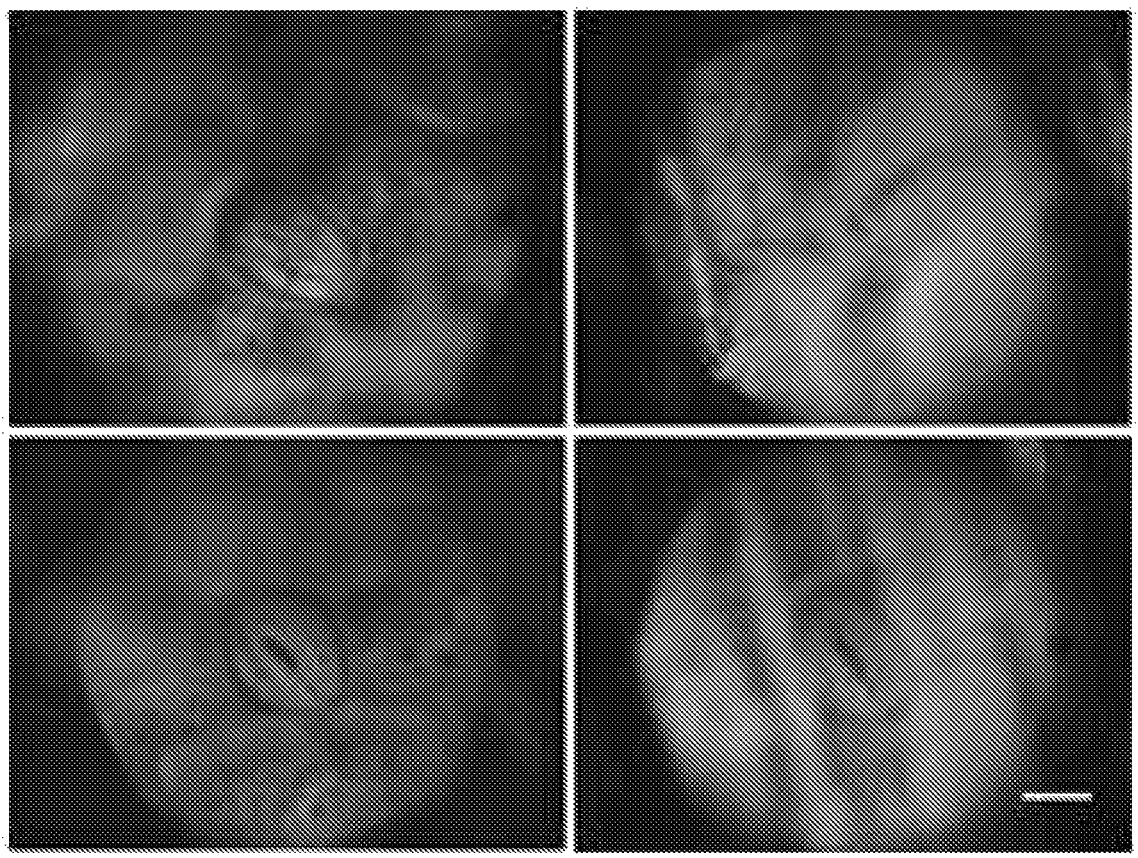
FIGS. 9A-9B show information about stomata.
Figure 9B:
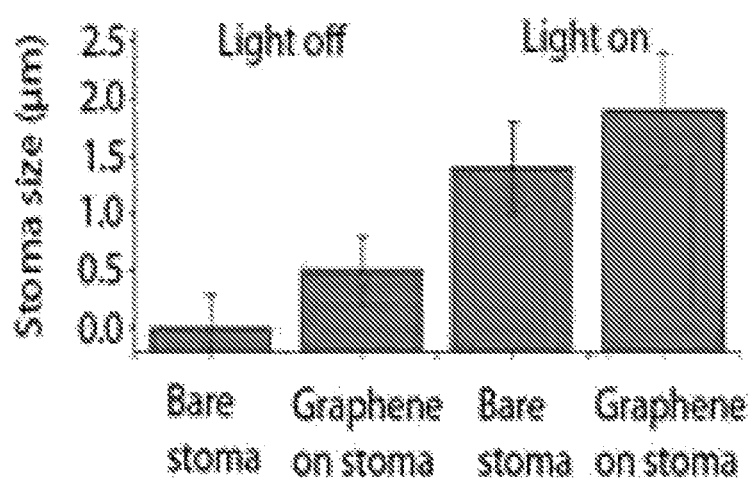
Figures 10A, 10B, 10C, 10D:
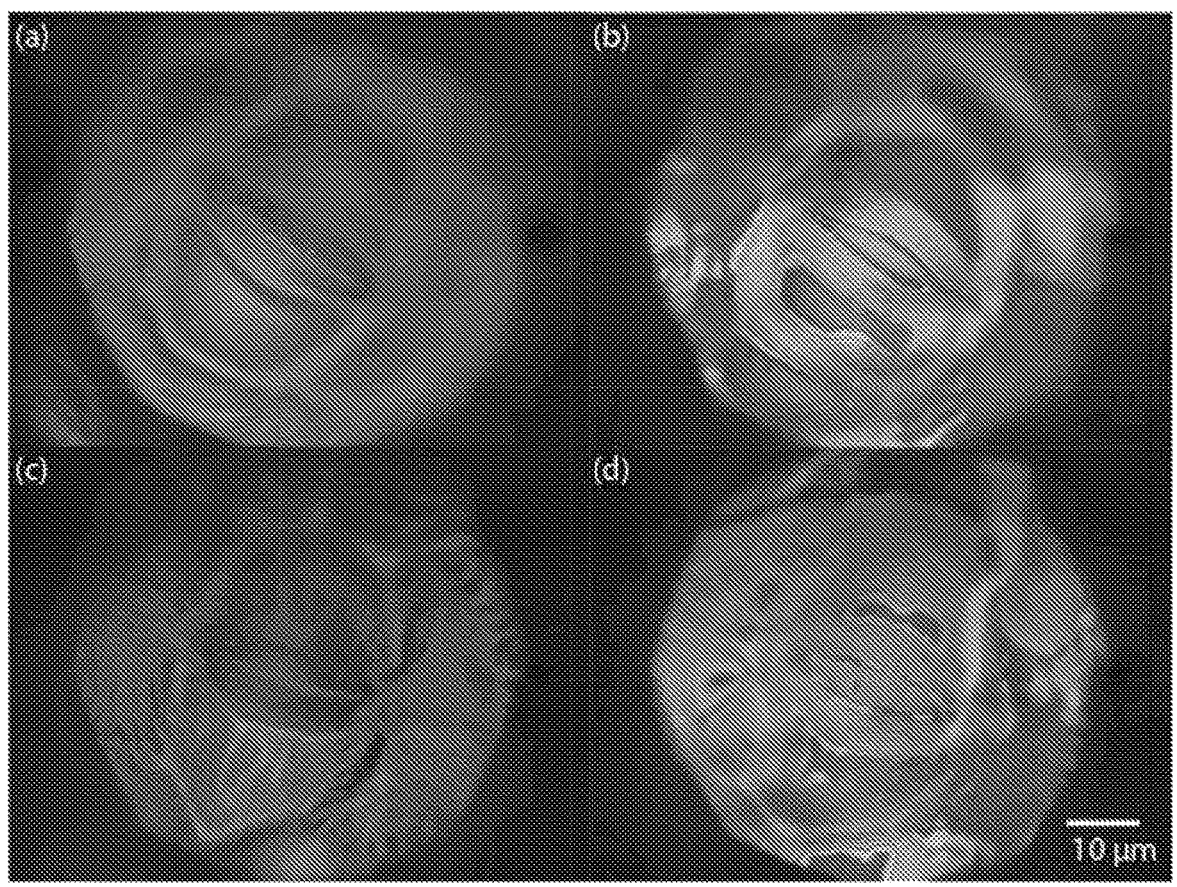
FIGS. 10A-10E show graphene-PMMA-Peace lily hybrid.
Figure 10E:
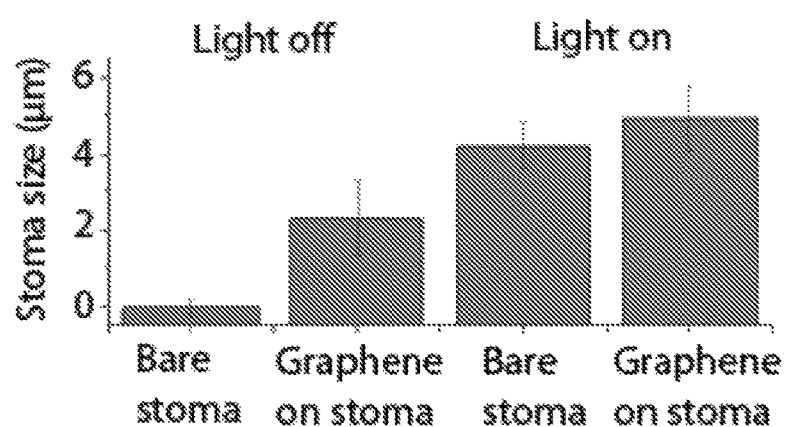

A nanobionic analyte sensing plant can be regulated via functionalization of the leaf surface and changing the leaf stomatal conductances (FIG. 8A). This was accomplished through the synthesis of a graphene-leaf hybrid material, where graphene-Poly(methyl methacrylate) (PMMA) is introduced on the abaxial side of the spinach leaf surface (FIG. 8B). The choice of graphene potentially allows two important functionalities: (1) as a transpiration regulator that can increase residence times of volatile analytes within the plant and (2) as a sensor in itself for volatile species that exits through the stomata together with water vapor, achieved via the analysis of doping trajectories of graphene. See, Paulus, G. L. C. et al. A graphene-based physiometer array for the analysis of single biological cells. *Scientific Reports* 4, 6865 (2014), which is incorporated by reference in its entirety. The introduction of graphene-PMMA layer maintains stomatal functionality (FIG. 9A), and interestingly maintains the stomata aperture at a larger mean size (0.3 µm larger) as compared to stomata on the exposed leaf surface (FIG. 9B). The same is observed of the Peace Lily plant (FIGS. 10A-10E). This hybrid material can change the detection limit of implanted sensors via extending or decreasing of analyte residence times, potentially allowing the plant to serve as a sensor for even low amounts of volatile analytes.

The viability of nanobionic plant detectors of nitroaromatics was assessed by monitoring changes in chlorophyll from leaf maturity to senescence (FIG. 4D). Leaves of three week old plants were infiltrated with B-SWCNT (8 mg/L), P-SWCNT (8 mg/L), and HEPES buffer (controls) and their chlorophyll content determined with a SPAD chlorophyll meter (Minolta). After five days of SWCNT infiltration, there were no changes in the chlorophyll content index. Then, a steady decline in chlorophyll was observed in control leaves and in SWCNT infiltrated leaves. There were no differences in the patterns of chlorophyll decline with leaf age among treatments indicating that the functionalized SWCNT sensors do not affect the leaf lifespan. SWCNT concentration was 8 mg/L. Error bars are standard deviations (n=5).

EXAMPLES

Materials

SWCNTs were purchased from Unidym (Lot #R1794). Bombolitin II (BLT2 structure NH2-SKITDILAKLGKV-LAHV-COOH) was purchased as synthesized from MIT Koch Integrative Center. The following were purchased form Sigma-Aldrich: Picric acid moistened with water ≥98%, Polyvinyl alcohol (PVA) (MW=31,000-50,000 98-99% hydrolyzed), potassium chloride, HEPES and Tris-buffer. Carmel spinach hybrid *Spinacia oleracea* and Farfard Professional all-purpose blend potting soil were purchased from David's Garden Seeds and Amazon Inc. respectively. Picric acid used in the reaction was prepared from a stock solution of saturated picric acid moistened with water ≥98%. This was then diluted in a 1:50 v/v ratio with DI water. Dopamine was purchased from Sigma Aldrich and diluted with DI water before use. $(GT)_{15}$ ssDNA was purchased from IDT (USA) and used as is.

Plant Growth

Carmel spinach (*Spinacia oleracea*) hybrid seeds purchased from David's Garden Seeds were planted in Farfard Professional all-purpose blend potting soil. Seeds were planted half an inch deep into soil of a standard six cell-seeding tray, with each cell measuring 1.5 in×2.3 in×3 in. The seeding tray was then placed in a light chamber for germination. The germinated plants were then moved to a Conviron Adaptis 1000 growth chamber under 2 umol m$^{-2}$ s$^1$ light levels, maintaining a 60-90% Relative Humidity (RH), daytime and night time temperatures of 18° C. and 22° C. respectively. Plants were allowed to mature to three weeks of age within the chamber before experimental use.

P-SWCNT, B-SWCNT and $(GT)_{15}$-SWCNT Preparation

For the preparation of P-SWCNTs, SWCNTs were first suspended in a 2 wt % sodium cholate (SC) aqueous solution. 1 mg/mL Unidym SWCNTs were added to 40 mL 2 wt % sodium cholate in water and were sonicated with a ⅛$^{th}$ inch probe tip at 40% amplitude (~12 W) for 1 hr in an ice bath. The resulting solution was centrifuged at 12800×g for 1 hr to remove unsuspended SWCNT aggregates and catalyst particles. 2 wt % of PVA solution was then added at a 1:1 v/v ratio with the sodium cholate—SWNT and the mixture was placed in a 12-14 kD MWCO dialysis bag and dialyzed against water for 24 hours to remove free sodium cholate and allow PVA to self-assemble on the nanotube surface.

B-SWCNTs were prepared as described elsewhere. See, Heller, D. A., et al. Peptide secondary structure modulates single-walled carbon nanotube fluorescence as a chaperone sensor for nitroaromatics. *Proc Natl Acad Sci* 108, 8544-8549 (2011), which is incorporated by reference in its entirety. Briefly, SWCNTs and Bombolitin were mixed in a 2:1 mass ratio in 20 mM Tris and 100 mM NaCl (pH=7.6). The mixture was sonicated using a ⅛$^{th}$ inch probe tip sonicator for 10 min. The resulting B-SWCNT solution was centrifuged for 11000×g for 40 min and the pellet was removed. $(GT)_{15}$-SWCNT were prepared as previously described by Kruss et al using (6,5) enriched SWCNTs. See, Kruss, S. et al. Neurotransmitter Detection Using Corona Phase Molecular Recognition on Fluorescent Single-Walled Carbon Nanotube Sensors. *J. Am. Chem. Soc.* 136, 713-724 (2014), which is incorporated by reference in its entirety.

Infiltration of Leaves with SWCNTs

Carmel spinach hybrid plants at three weeks old, with healthy leaves, were selected. The plants were prepared by first gently rinsing the roots with 10 mM KCl buffer and wrapping the roots in buffer-moistened cheese cloth to keep the plants hydrated, before transplanting the plant into a small 50 mL beaker. 1:1 Aliquots of P-SWCNTs and B-SWCNTs were prepared by mixing P-SWCNT or B-SWCNT respectively and 1 µl HEPES buffer. A leaf from the plant was then infiltrated as in Huang et. al. See, Huang, X., et al. Magnetic virus-like nanoparticles in *N benthamiana* plants: a new paradigm for environmental and agronomic biotechnological research. *ACS Nano.* 5, 4037-4045 (2011), which is incorporated by reference in its entirety. A 1 mL needleless syringe was used push the SWCNT solution through several areas on the abaxial side of the leaf lamina, with P-SWCNT on the left side of the mid rib and B-SWCNT on the right side of the mid rib to ensure no mixing of SWCNTs. The underside of the leaf was then thoroughly rinsed with water to ensure that there are no SWCNTs on the surface of the leaf. Plants were allowed to sit for 30 mins before imaging Picric Acid Detection Via Root Uptake (i) Laboratory Demonstration For the laboratory demonstration of standoff detection of nitroaromatics via root uptake, a whole spinach plant was prepared as described earlier and set up as shown in FIG. 2A. A FEL 0900 nm long pass filter was purchased from Thorlab Inc and placed in front of a Princeton Instruments OMA V InGaAs detector, equipped with a Nikon AF Micro-Nihhor 60 mm f/2.8D lens. The nIR fluorescence intensity of embedded SWCNTs under laser excitation (785 nm, 15 mW) was monitored throughout the experiment at a distance of 0.85 m. Picric acid (400 µM) was introduced via a pipette at the start of the experiment, and the nIR fluorescence of both B-SWCNTs and P-SWCNTS (bright field images seen in FIG. 2B were monitored at 1-minute intervals for >80 mins.

(ii) Minaturized System with RaspberryPi

A Raspberry Pi® equipped with a f=3.6 mm 1/2.7" CCD detector with IR filters removed (SainSmart Infrared Night Vision Surveillance Camera, KS, USA) was used. To detect nIR emission from the SWCNT sensors embedded within the living plant (under laser excitation (785 nm, 15 mW)), a FEL0750 long pass filter (ThorLabs Inc.) was placed in front of the camera lens, and images were collected at 6 s exposure with ISO 800. The RaspberryPi was WIFI enabled to allow for images to be sent in real time to the user's smartphone.

Dopamine Detection Via Root Uptake

A leaf of a healthy spinach plant was selected and infiltrated with $(GT)_{15}$-SWCNT using the protocol previously described. For spectrometry of leaves with infiltrated SWNTs, the Axiovision Zeiss inverted microscope (Zeiss, Axiovert 200), 20× objective was coupled to an InGaAs array detector (OMA-V, Princeton Instruments) through an Acton SP-2500 spectrograph (Princeton Instruments). Infiltrated SWNTs were excited with a 785 nm Invictus photodiode laser excitation (Kaiser) through the leaf lamina. 100 µM of Dopamine solution was introduced to the roots and spectrums were acquired at a frame rate of 1 frame/minute, at a 2 s exposure time.

Picric Acid Detection Via Cuticle Uptake

A spinach leaf was functionalized as previously described and gently held by double-sided tape on the adaxial side while the leaf abaxial side was exposed to 785 nm laser excitation, in a similar set up as shown in FIG. 2A. 0.2 mL of 0.4 mM picric acid was deposited on the leaf surface leading to droplet movement downwards by gravitational pull. The nIR fluorescence intensity of the leaf under laser excitation was monitored throughout the experiment with a Princeton Instruments OMA V detector, at a distance of 0.85 m.

Graphene Growth and Transfer onto PMMA

Large-area monolayer graphene films were grown by a modified CVD method (CVD-graphene) on copper foils. Typically, a ~4 cm$^2$ (2×2 cm) Cu foil (Aldrich, 99.999%, 25 μm thick) was placed at the center of a 1-inch-diameter fused quartz tube in a tube furnace. The furnace tube was evacuated and heated to 1000° C. under a 30 sccm H$_2$ gas flow with a pressure of ~650 mTorr. After annealing for 30 min, a CH$_4$ gas flow of 0.50 sccm was introduced and the temperature in the furnace tube was maintained for 15 min. The CH$_4$ gas flow was stopped after the growth period and the temperature maintained at 1000° C. for another 5 min. The Cu foil was then cooled to room temperature under H$_2$ gas flow.

For the transfer of graphene onto PMMA solution (950PMMA, A4, MicroChem) was spin-coated (3000 rpm, 1 min) onto the CVDG/Cu foil (2×2 cm), supported on a glass substrate. After drying at room temperature for 10 min, the PMMA-coated CVDG/copper was annealed at 100° C.'C for 10 min, then removed and cooled to room temperature. The Cu foil was etched by Copper Etchant APS-100 (Transene Co. Inc.) at 30° C. overnight with CVDG/PMMA film suspending in the blue etchant solution. The film was transferred out from the solution by using Si/SiO$_2$ wafer and rinsed with Milli-Q water four times (10 min each time), before being suspended in Milli-Q water.

Graphene-PMMA Transfer onto Leaf Surface and Stomata Aperture Measurements

Two wild type species, *Spinacia oleracea* (spinach) and *Spathilphyllum cochlearispathum* (Peace lily) were used. All experiments were conducted at 23° C. and 30% humidity with plants being well watered. To transfer graphene on leaf surface, a drop of water was first deposited on the leaf, before graphene was gently introduced onto the water meniscus. Plants were left for 24 hours for water to evaporate from the graphene-leaf surface. Images of stomata aperture were obtained in reflection mode using 100× air objective (Zeiss, A-Plan 100×/0.8 M27). To open stomata, plants were exposed to 10 mW/cm$^2$ white light lamp (Sinostar, FL-70W) for 2 hours.

Pre-Concentration Calculations

The degree of pre-concentration of picric acid in the leaf can be calculated considering a typical mass balance equation relating the mass flow rate of inputs ($m_{in}$), outputs ($m_{out}$), generation ($m_{gen}$), consumption ($m_{consump}$) and accumulation ($m_{acc}$):

$$m_{in} - m_{out} + m_{gen} - m_{consump} = m_{acc}$$

It is assumed that the volatility of picric acid (BP>300° C.) is sufficiently low such that it does not escape the plant via the stomata or leaf cuticle (i.e. out=0 mol/min). There is also no picric acid generated by the natural biochemical processes of the *Spinacia oleracea* plant.

$$m_{in} - m_{consump} = m_{acc}$$

It is assumed that the rate of decomposition or consumption is much lower (half-life of TNT is approximately 20 hrs in the aquatic *Myriophyllum spicatum* plant; see Pavlostathis, S. G., Comstock, K. K., Jacobson, M. E. & Saunders, F. M. Transformation of 2,4,6-Trinitrotoluene by the aquatic plant *Myriphyllum spicatum. Environ. Toxicol. Chem.* 17, 2266-2273 (1998), which is incorporated by reference in its entirety) than the rate of uptake through the roots. i.e.:

$$m_{in} = m_{acc}$$

where $m_{in}$ may be regarded as a function of [picric acid] in soil, root permeability and flow rate of into the roots.

Schneider and co workers reported that the plant root concentration of nitroaromatics at short times upon exposure to 100 mg/kg DW soil was approximately 1 mg/kg DW, corresponding to an permeability of approximately 0.01 (i.e. permeability ratio). See, Schneider, K., Oltmanns, J., Radenberg, T., Schneider, T. & Mundegar, D. Uptake of nitroaromatic compounds in plants. *Environ. Sci. & Pollut. Res.* 3, 135-138 (1996), which is incorporated by reference in its entirety. Furthermore, the permeability ratio is dependent on the concentration of nitroaromatics in the soil—at low concentrations of 1 mg/kg nitroaromatics in soil, the permeability ratio in the roots becomes 0.5. They also reported that the concentration of nitroaromatics in the leaves and stems amounted to approximately 20% of the corresponding root concentration in the plants investigated (e.g. Kale, Bush Beans, Lettuce, Radish). At long times of >7 days, it is known that plants can significantly bioaccumulate explosive compounds. Thompson et al reported that leaf tissues contained 97 mg/kg of RDX at 7 days (vs 19 mg/kg) after exposure to 10 mg/L of RDX. See, Thompson, P., Ramer, L. & Schnoor, J. Hexahydro-1,3,5-trinitro-1,3,5-triazine translocation in poplar trees. *Env. Toxicology* 18, 279-284 (1999), which is incorporated by reference in its entirety. Plant extractions also resulted in mass balances that averaged 79.7% recovery from the soil. Similarly, Pennington and Brannon[44] reported that when grown in soil contaminated with 58 mg/kg RDX, lettuce was found to contain 1,200 mg/kg of RDX, demonstrating accumulation of nitroaromatic compounds in plants.

Using an approximate maximum flow rate up the plant of 1.6 mL/min, and a [picric acid] of 400 μM (or approximately 90 mg/kg water), the accumulation rate in the roots (permeability ratio 0.01) can be estimated to be 0.0064 umol/min and correspondingly the accumulation rate in the leaf is estimated to be 1.28 nmol/min. Using a soil nitroaromatic concentration of 1 mg/kg DW soil (root permeability ratio 0.5) would yield an approximate accumulation rate of 0.7 nmol/min. However, this value is only an estimate and depends strongly upon the permeability of nitroaromatics through the roots, which is dependent upon the species, age of the plant, and hydration or weather conditions.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed is:

1. A sensor for an analyte comprising:
   a first channel including a first complex including a nanoparticle and a first polymer, wherein the first channel detects a stimulus within a plant; and
   a second channel including a second complex including a nanoparticle and a second polymer, wherein the second channel detects a reference property within the plant.

2. The sensor for an analyte of claim 1, wherein the first polymer adsorbed on the nanostructure has a selective binding site and the polymer is free from selective binding to an analyte in the absence of being adsorbed on the nanostructure.

3. The sensor for an analyte of claim 1, wherein the nanostructure is a photoluminescent nanostructure.

4. The sensor for an analyte of claim 3, wherein the photoluminescent nanostructure is a nanotube, a carbon nanotube, a single-walled carbon nanotube, or graphene.

5. The sensor for an analyte of claim 1, wherein the first polymer is Bombolitin.

6. The sensor for an analyte of claim 1, wherein the first polymer is a polysaccharide.

7. The sensor for an analyte of claim 6, wherein the polysaccharide includes dextran, a functionalized dextran, phenoxy functionalized dextran, or boronic acid functionalized phenoxy dextran.

8. The sensor for an analyte of claim 1, wherein the first polymer is a polynucleotide.

9. The sensor for an analyte of claim 8, wherein the polynucleotide has an ordered sequence, or is poly(AT), poly(GT), poly(CT), poly(AG), poly(CG), or poly(AC).

10. The sensor for an analyte of claim 1, wherein the first polymer is a polypeptide.

11. The sensor for an analyte of claim 10, wherein the polypeptide includes a mastoparan, mastoparan 7, or mastoparan X.

12. The sensor for an analyte of claim 1, wherein the first polymer is a polylipid.

13. The sensor for an analyte of claim 12, wherein the polylipid includes a phospholipid, a palmitoyl phospholipid, or 1,2-dipalmitoyl-sn-glycero-3-phosphoethanolamine-N-(lauroyl).

14. The sensor for an analyte of claim 1, wherein the first polymer is polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

15. The sensor for an analyte of claim 1, wherein the first polymer is a dye conjugate or a branched polymer.

16. The sensor for an analyte of claim 1, wherein the second polymer is polyvinylpyrrolidone, poly(ethylene oxide)-poly(propylene oxide)-poly(ethyleneo oxide) block co-polymer, a poly(ethylene oxide), poly(N-isopropyl acrylamide), polyethyleneimine, polyacrylamide, polyvinyl alcohol or collagen.

17. The sensor for an analyte of claim 2, the stimulus is a concentration of the analyte.

18. The sensor for an analyte of claim 17, wherein the analyte is a monosaccharide, a polysaccharide, an amino acid, a nucleotide, an oligonucleotide, a lipid, a polylipid, a steroid, a peptide, a protein, riboflavin, nitric oxide, or nitroaromatic.

19. The sensor for an analyte of claim 17, wherein the analyte is 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramine, urea, or picric acid.

20. The sensor of claim 1, wherein the plant is a wild-type plant.

21. A green plant including the sensor of claim 1.

22. A method for analyzing a sample for an analyte, comprising:
providing a sensor comprising
a first channel including a first complex including a nanoparticle and a first polymer, wherein the first channel detects a stimulus within a plant; and
a second channel including a second complex including a nanoparticle and a second polymer, wherein the second channel detects a reference property within the plant;
exposing the sensor to a sample;
monitoring a first signal of the first channel and a second signal of the second channel; and
determining a presence of the analyte in the sample based on the first signal and the second signal.

23. The method of claim 22, wherein the sample includes a gas, a liquid or a solid.

24. The method of claim 22, wherein the sample is a ground water.

25. The method of claim 22, wherein the sample is a biological fluid.

26. The method of claim 22, wherein the first signal is an emission, emission intensity, or an emission wavelength.

27. The method of claim 26, wherein the emission is infrared (IR) fluorescent emission.

28. The method of claim 22, wherein the second signal is an emission, emission intensity, or an emission wavelength.

29. The method of claim 28, wherein the emission is infrared (IR) fluorescent emission.

30. The method of claim 22, wherein exposing the composition to a sample includes inserting the composition into an animal, a plant, or a fungus.

31. The method of claim 22, wherein exposing the composition to a sample includes incubating the composition with a microorganism, a virus, a cell line, or an in vitro model system.

32. The method of claim 22, wherein determining the presence of an analyte includes determining the absence of the analyte, or determining the concentration of the analyte.

33. The method of claim 22, wherein monitoring the first signal of the first channel and the second signal of the second channel is performed using a high-throughput system.

34. The method of claim 22, wherein the composition is exposed to a sample in a well in a well plate array.

35. The method of claim 22, wherein monitoring the first signal of the first channel and the second signal of the second channel is executed by a satellite.

36. The method of claim 22, wherein monitoring the first signal of the first channel and the second signal of the second channel is executed from a distance of several meters.

37. The method of claim 22, wherein monitoring the first signal of the first channel and the second signal of the second channel is executed from a distance of tens of meters.

38. The method of claim 22, wherein monitoring the first signal of the first channel and the second signal of the second channel is executed from a distance of hundreds of meters.

39. The method of claim 22, wherein the first signal and second signal is sent to a cell phone.

40. A method for analyzing a sample for a plurality of analytes, comprising:
providing a plurality of sensors, wherein each sensor comprising
a first channel including a first complex including a nanoparticle and a first polymer, wherein the first channel detects a stimulus within a plant; and a second channel including a second complex including a nanoparticle and a second polymer, wherein the second channel detects a reference property within the plant;

exposing the plurality of the sensors to a sample;

monitoring a first signal of the first channel of the each sensor and a second signal of the second channel of the each sensor; and determining a presence of each analyte in the sample based on the first signal and the second signal of the each sensor.

41. A sensor for an analyte comprising:

a first channel including a first complex including graphene and a first polymer, wherein the first channel detects a stimulus within a plant; and a second channel including a second complex including graphene and a second polymer, wherein the second channel detects a reference property within the plant.

42. A method for analyzing a sample for an analyte, comprising:

providing a sensor comprising a first channel including a first complex including graphene and a first polymer, wherein the first channel detects a stimulus within a plant; and a second channel including a second complex including graphene and a second polymer, wherein the second channel detects a reference property within the plant;

exposing the sensor to a sample;

monitoring a first signal of the first channel and a second signal of the second channel; and determining a presence of the analyte in the sample based on the first signal and the second signal.

43. A method for analyzing a sample for a plurality of analytes, comprising:

providing a plurality of sensors, wherein each sensor comprising a first channel including a first complex including graphene and a first polymer, wherein the first channel detects a stimulus within a plant; and a second channel including a second complex including graphene and a second polymer, wherein the second channel detects a reference property within the plant;

exposing the plurality of the sensors to a sample;

monitoring a first signal of the first channel of the each sensor and a second signal of the second channel of the each sensor; and determining a presence of each analyte in the sample based on the first signal and the second signal of the each sensor.

\* \* \* \* \*